(12) United States Patent
Manam et al.

(10) Patent No.: US 12,391,724 B2
(45) Date of Patent: Aug. 19, 2025

(54) POLYPODOSIDE SWEET FLAVOR MODIFIER

(71) Applicant: Firmenich Incorporated, Plainsboro, NJ (US)

(72) Inventors: Rama Rao Manam, San Diego, CA (US); Nicole Servant, San Diego, CA (US); Andrew P. Patron, San Marcos, CA (US); Christina Susanto, San Diego, CA (US); Emilia Avanes, Burbank, CA (US)

(73) Assignee: Firmenich Incorporated, Plainsboro, NJ (US)

( * ) Notice: Subject to any disclaimer, the term of this patent is extended or adjusted under 35 U.S.C. 154(b) by 670 days.

(21) Appl. No.: 17/291,814

(22) PCT Filed: Apr. 1, 2020

(86) PCT No.: PCT/US2020/026097
§ 371 (c)(1),
(2) Date: May 6, 2021

(87) PCT Pub. No.: WO2020/205922
PCT Pub. Date: Oct. 8, 2020

(65) Prior Publication Data
US 2021/0388021 A1     Dec. 16, 2021

Related U.S. Application Data

(60) Provisional application No. 62/828,906, filed on Apr. 3, 2019.

(51) Int. Cl.
*C07J 17/00*     (2006.01)
*A23L 27/30*     (2016.01)

(52) U.S. Cl.
CPC ............. *C07J 17/005* (2013.01); *A23L 27/36* (2016.08)

(58) Field of Classification Search
CPC .................................................. C07J 17/005
See application file for complete search history.

(56) References Cited

U.S. PATENT DOCUMENTS

| 9,101,161 B2 * | 8/2015 | Prakash | A23L 2/52 |
| 2008/0107787 A1 * | 5/2008 | Prakash | A61P 3/10 |
| | | | 426/548 |

OTHER PUBLICATIONS

Kim et al., Phytochem. vol. 28, No. 4, pp. 1225-1228, 1989.*
Nishiza et al., Chemistry Letters, pp. 155-158, (1994).*
Kim et al., Jan. 1989, Further steroidal and flavonoid constituents of the sweet plant, polypodium glycyrrhiza, Phytochemistry, 28(4):1225-1228.
Nishizawa et al., Aug. 1994, Structure revision of polypodoside A. major sweet principle of polypodium glycyrrhiza, Chemistry Letters, 23(8):1555-1558.
Nishizawa et al., Feb. 18, 1994, Synthesis and structure revision of intensely sweet saponin, osladin, Journal of the Indian Institute of Science, 74(1):169-179.
International Search Report and Written Opinion dated Jul. 23, 2020 in application No. PCT/US2020/026097.
Meilgaard et al., 1999, Chapter 1: Introduction to sensory techniques, in Sensory Evaluation Techniques. 3rd edition, CRC Press, Boca Raton.
Morel et al., 1951, Fern Callus Tissue Culture, American Journal of Botany, 38(2): 141-143.
Royal Botanic Garden Edinburgh (RBGE) (2007): Digital Flora Europaea: Polypodium species list.
Smith et al., May 2003, GRAS Flavoring Substances 21, Food Technology, 57(5):46-59.
Tunaley, 1989, Perceptual Characteristics of Sweeteners, in Progress in Sweeteners, Grenby, ed. Elsevier Applied Science, pp. 291-309.
United States Department of Agriculture, Germplasm Resources Information Network Polypodium, downloaded from https://npgsweb.ars-grin.gov/gringlobal/search, on Nov. 13, 2023, 3 pp.
Wiet et al., May-Jun. 1993, Fat concentration affects sweetness and sensory profiles of sucrose, sucralose, and aspartame, J. Food Sci., 58(3):599-602.
Wikipedia, Nov. 11, 2020, Polypodiuym glycyrrhiza, downloaded from <https://web.archive.org/web/20201111222741/https://en.wikipedia.org/wiki/Polypodium_glycyrrhiza> 4 pp.

* cited by examiner

*Primary Examiner* — Paul V Ward
(74) *Attorney, Agent, or Firm* — Knobbe, Martens, Olson & Bear, LLP

(57) ABSTRACT

The present invention includes compounds having structural formula (I), wherein R1-R9 are as defined herein, or salts or solvates thereof. These compounds are useful as sweet flavor modifiers. The present invention also includes compositions comprising the present compounds and methods of enhancing the sweet taste of compositions.

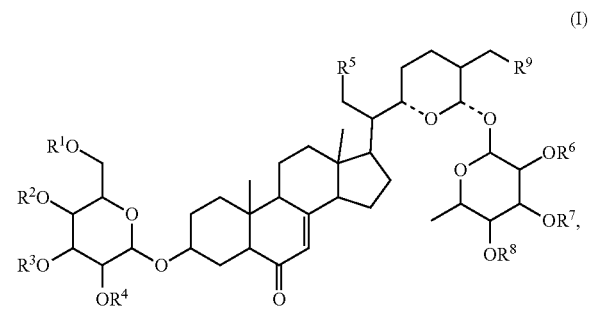

(I)

14 Claims, No Drawings

POLYPODOSIDE SWEET FLAVOR MODIFIER

CROSS-REFERENCE TO RELATED APPLICATIONS

This application is a U.S. National Phase of International Patent Application No. PCT/US2020/026097, filed on Apr. 1, 2020, and published on Oct. 8, 2020, as WO 2020/205922, which claims the benefit of U.S. Provisional Patent Application No. 62/828,906, filed on Apr. 3, 2019, the contents of which are hereby incorporated by reference in their entireties for all purposes.

BACKGROUND

Field

The invention relates to isolated or purified polypodoside compounds and extracts from a plant in the *Polypodium* genus, such as *Polypodium glycyrrhiza* suitable for modifying sweet flavor.

Background Description

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Mammals are believed to have five basic taste modalities: sweet, bitter, sour, salty, and umami (the taste of monosodium glutamate, a.k.a. savory taste).

Obesity, diabetes, and cardiovascular disease are health concerns on the rise globally, but are growing at alarming rates in the United States. Sugar and calories are key components that can be limited to render a positive nutritional effect on health. High-intensity sweeteners can provide the sweetness of sugar, with various taste qualities. Because they are many times sweeter than sugar, much less of the sweetener is required to replace the sugar.

High-intensity sweeteners have a wide range of chemically distinct structures and hence possess varying properties, such as, without limitation, odor, flavor, mouthfeel, and aftertaste. These properties, particularly flavor and aftertaste, are well known to vary over the time of tasting, such that each temporal profile is sweetener-specific (Tunaley, A., "Perceptual Characteristics of Sweeteners", Progress in Sweeteners, T. H. Grenby, Ed. Elsevier Applied Science, 1989).

Sweeteners such as saccharin and 6-methyl-1,2,3-oxathiazin-4(3H)-one-2,2-dioxide potassium salt (acesulfame potassium) are commonly characterized as having bitter and/or metallic aftertastes. Products prepared with 2,4-dihydroxybenzoic acid are claimed to display reduced undesirable aftertastes associated with sweeteners, and do so at concentrations below those concentrations at which their own tastes are perceptible. Also, high intensity sweeteners such as sucralose and aspartame are reported to have sweetness delivery problems, i.e., delayed onset and lingering of sweetness (S. G. Wiet, et al., J. Food Sci., 58(3):599-602, 666, 1993).

Thus, there is a need in the art to develop novel sweet flavor modifiers.

SUMMARY

In one embodiment, the present invention provides an isolated or purified compound having structural Formula (I):

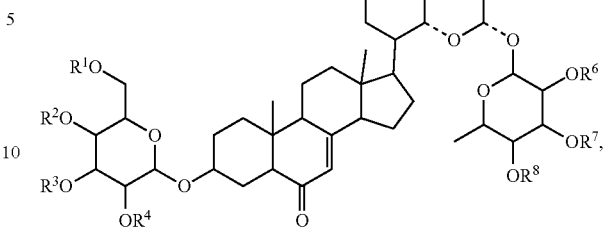

or a salt or solvate thereof; wherein $R^1$, $R^2$, $R^3$, $R^4$, $R^6$, $R^7$, and $R^8$ are independently hydrogen, alkyl, heterocyclyl, or substituted heterocyclyl; and $R^5$ and $R^9$ are independently hydrogen, hydroxyl, alkoxy, heterocyclyl, or substituted heterocyclyl.

In one embodiment, the present invention provides an extract of a plant in the *Polypodium* genus such as *Polypodium glycyrrhiza* comprising one or more compounds having structural Formula (I):

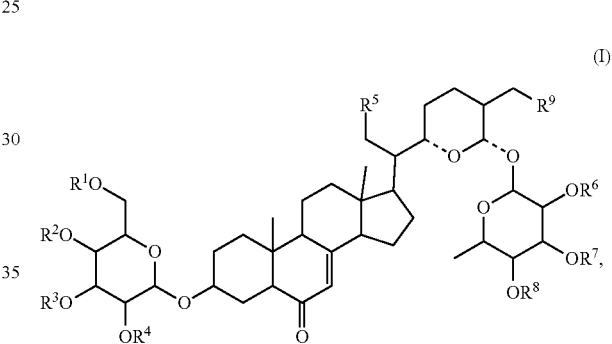

or a salt or solvate thereof; wherein $R^1$, $R^2$, $R^3$, $R^4$, $R^6$, $R^7$, and $R^8$ are independently hydrogen, alkyl, heterocyclyl, or substituted heterocyclyl; and $R^5$ and $R^9$ are independently hydrogen, hydroxyl, alkoxy, heterocyclyl, or substituted heterocyclyl; and wherein the extract is suitable for human or animal consumption.

In another embodiment, the present invention provides an ingestible composition comprising an isolated or purified compound or the extract of the present invention; and optionally an ingestibly acceptable excipient.

In another embodiment, the present invention provides a method of modifying the sweet taste of a composition comprising contacting the composition thereof with an isolated or purified compound or the extract of the present invention to form a sweet taste modified composition. In the method, the present compound can be a chemosensory receptor modifier, a chemosensory receptor ligand modifier, or both, i.e., a partial chemosensory receptor modifier and partial chemosensory receptor ligand modifier. For example, the present compound can be a sweet receptor agonist, or a sweet enhancer, or a partial sweet receptor agonist and partial sweet enhancer.

In another embodiment, the present invention provides a flavoring concentrate formulation comprising i) as flavor modifying ingredient, an isolated or purified compound or the extract of the present invention; ii) a carrier; and iii) optionally at least one adjuvant.

DETAILED DESCRIPTION

The present invention relates generally to isolated sweet flavor modifying compounds; compositions comprising those isolated compounds; and methods for isolating and using them. In one embodiment, these isolated compounds are non-caloric or low-caloric high-potency natural sweeteners. In one embodiment, the present invention relates to the identification of several novel polypodoside analogs that can activate the sweet receptor in vitro and impart a sweet taste in sensory studies. The isolated sweet flavor modifying compounds of the present invention can be used in a variety of ingestible compositions. In one embodiment, the ingestible composition comprises at least one isolated sweet flavor modifying compound of the present invention. In another embodiment, the ingestible composition further comprises one or more sweeteners, which can be a natural sweetener, e.g., sucrose; a synthetic high-potency sweetener, e.g., sucralose. The present invention also relates to compositions and methods that can improve the tastes of non-caloric or low-caloric natural and/or synthetic, high-potency sweeteners by imparting a more sugar-like taste or characteristic by utilizing a new novel natural sweetener in conjunction with other sweeteners natural or synthetic. In one embodiment, the sweetener compositions and methods provide a more sugar-like temporal profile, including sweetness onset and sweetness linger, and/or a more sugar-like flavor profile.

These and other embodiments, advantages, and features of the present invention are provided in the sections below. Unless defined otherwise, all technical and scientific terms used herein have the same meaning as commonly understood by one of ordinary skill in the art to which this invention belongs.

Definitions

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" includes "cycloalkyl" as defined herein below. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 12 carbon atoms ($C_1$-$C_{12}$ alkyl). In still other embodiments, an alkyl group comprises from 1 to 6 carbon atoms ($C_1$-$C_6$ alkyl). It is noted that when an alkyl group is further connected to another atom, it becomes an "alkylene" group. In other words, the term "alkylene" refers to a divalent alkyl. For example, —$CH_2CH_3$ is an ethyl, while —$CH_2CH_2$— is an ethylene. That is, "Alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined herein below. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanylene," "alkenylene," and "alkynylene" are used. In some embodiments, an alkylene group comprises from 1 to 20 carbon atoms ($C_1$-$C_{20}$ alkylene). In other embodiments, an alkylene group comprises from 1 to 12 carbon atoms ($C_1$-$C_{12}$ alkylene). In still other embodiments, an alkylene group comprises from 1 to 6 carbon atoms ($C_1$-$C_6$ alkylene).

"Alkanyl," by itself or as part of another substituent, refers to a saturated branched, straight-chain or cyclic alkyl radical derived by the removal of one hydrogen atom from a single carbon atom of a parent alkane. The term "alkanyl" includes "cycloakanyl" as defined herein below. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The term "alkenyl" includes "cycloalkenyl" as defined herein below. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, refers to a radical of the formula —O—$R^{199}$, where $R^{199}$ is alkyl or substituted alkyl as defined herein.

"Acyl" by itself or as part of another substituent refers to a radical —$C(O)R^{200}$, where $R^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl), i.e., 6- to 20-membered aryl ring. In other embodiments, an aryl group comprises from 6 to 15 carbon atoms ($C_6$-$C_{15}$ aryl), i.e., 6- to 15-membered aryl ring. In still other embodiments, an aryl group comprises from 6 to 15 carbon atoms ($C_6$-$C_{10}$ aryl), i.e., 6- to 10-membered aryl ring.

"Arylalkyl" or "aralkyl" by itself or as part of another substituent, refers to an acyclic alkyl group in which one of the hydrogen atoms bonded to a carbon atom, typically a terminal or $sp^3$ carbon atom, is replaced with an aryl group as, as defined herein. That is, an arylalkyl or aralkyl group is composed of an aryl group connected to an alkylene group which is further attached to other portion of a molecule. The alkylene group in the arylalkyl or aralkyl group can be an alkylene having 1 to 12 carbon atoms, or 1 to 6 carbon atoms, or 1 to 3 carbon atoms. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Cycloalkyl," or "Carbocyclyl," by itself or as part of another substituent, refers to a saturated or unsaturated cyclic alkyl radical, as defined herein. Similarly, "Cycloalkylene," or "Carbocyclylene," by itself or as part of another substituent, refers to a saturated or unsaturated cyclic alkylene radical, as defined herein. Where a specific level of saturation is intended, the nomenclature "cycloalkanyl", "cycloalkenyl", or "cycloalkynyl" is used. Typical cycloalkyl groups include, but are not limited to, groups derived from cyclopropane, cyclobutane, cyclopentane, cyclohexane, and the like. In some embodiments, the cycloalkyl group comprises from 3 to 10 ring atoms ($C_3$-$C_{10}$ cycloalkyl). In other embodiments, the cycloalkyl group comprises from 3 to 7 ring atoms ($C_3$-$C_7$ cycloalkyl). The cycloalkyl may be further substituted by one or more heteroatoms including, but not limited to, N, P, O, S, and Si, which attach to the carbon atoms of the cycloalkyl via monovalent or multivalent bond.

By "extract", it is meant a substance or mixture that has been taken from a plant by at least one purification or other processing step. The "plant", as used herein, includes but is not limited to a whole plant, a plant part, a plant tissue, a plant cell, or a combination thereof. In some embodiments, the plant is a fern. In some embodiments, the fern is a plant in the *Polypodium* genus, such as licorice fern (i.e., *Polypodium glycyrrhiza*). In one embodiment, the extract comprises one or more compounds having structural Formula (I), (Ia), or any subgenera or species thereof as described herein. In some embodiments, the extract is obtained from a plant, a plant part, a plant tissue or a plant cell of a plant in the *Polypodium* genus. In some embodiments, the extract is obtained from rhizomes of the plant.

"Plant part" or "plant tissue" refers to any part of a plant. Examples of plant parts include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, spores, stolon, shoot, pericarp, endosperm, placenta, berry, stamen, and leaf sheath.

"Fern" refers to a plant in the class of Cladoxylopsida, Psilotopsida, Equisetopsida (alias Sphenopsida), Marattiopsida, Polypodiopsida (alias Pteridopsida, Filicopsida), Zygopteridales, Stauropteridales, or Rhacophytales. Ferns are vascular plants differing from lycophytes by having true leaves (megaphylls), which are often pinnate. They differ from seed plants (gymnosperms and angiosperms) in their mode of reproduction for lacking flowers and seeds. Like all other vascular plants, they have a life cycle referred to as alternation of generations, characterized by alternating diploid sporophytic and haploid gametophytic phases. The gametophyte of ferns is a free-living organism, whereas the gametophyte of the gymnosperms and angiosperms is dependent on the sporophyte.

"*Polypodium*" refers to the genus of true ferns, a.k.a. holly ferns. Fern plants in the *Polypodium* genus can be terrestrial or epiphytic ferns. Plants in the *Polypodium* genus usually have a creeping, densely hairy or scaly rhizome bearing fronds at intervals along its length. The species may differ in size and general appearance and in the character of the fronds, which are evergreen, persisting for 1-2 years, pinnate or pinnatifid, and from about 10 cm to about 80 cm or longer. The sori or groups of spore-cases (sporangia) are borne on the back of the frond; they are globose and naked, not covered with a membrane (indusium). A plant within the *Polypodium* genus can be haploid, diploid or polyploid. The plant can be either a pure line (e.g., an inbred line) or a hybrid line derived from two or more plant species. In some embodiments, at least one species is in the *Polypodium* genus. In some embodiments, all parent species are in the *Polypodium* genus. In some embodiments, at least one parent plant is *Polypodium glycyrrhiza*. In some embodiments, the plant is *Polypodium glycyrrhiza*. In some embodiments, the plant is a specific variety or cultivar of a *Polypodium* species. In some embodiments, the plant is a offspring of a plant in the *Polypodium* genus, such as *Polypodium glycyrrhiza*. In some embodiments, the plant is derived from a cross between two or more fern plants, wherein at least one parent plant is in the *Polypodium* genus, such as *Polypodium glycyrrhiza*.

In some embodiments, the plant is selected from the group consisting of *Polypodium abitaguae, Polypodium alfredii, Polypodium amorphum* Suksdorf (irregular polypody), *Polypodium appalachianum*, (Haufler & Windham—Appalachian rockcap fern), *Polypodium argyrolepis, Polypodium asterolepis* Baker, *Polypodium billardieri, Polypodium californicum* Kaulf, *Polypodium calirhiza* (nested polypody, habit polypody), *Polypodium cambricum* L. (i.e., *P. australe* Fée—southern polypody), *Polypodium chionolepis, Polypo-*

*dium decumanum* (i.e., Calaguala fern), *Polypodium excavatum* Roxb., *Polypodium exiguum* (i.e., hug-me-tight), *Polypodium feei* (Bory) Mett., *Polypodium* x font-*queri* (*P. cambricum* x *P. vulgare*), *Polypodium formosanum* Baker (i.e., grub fern), *Polypodium furfuraceum* Schltdl. & Cham, *Polypodium glycyrrhiza* (i.e., licorice fern), *Polypodium hesperium* Maxon (western polypody), *Polypodium incanum, Polypodium* x *incognitum, Polypodium interjectum* Shivas (intermediate polypody), *Polypodium latissimum, Polypodium lepidopteris* (Langsd. & Fisch.) Kunze, *Polypodium macaronesicum* Bobrov, *Polypodium* x *mantoniae* (*P. interjectum* x *P. vulgare*), *Polypodium mindense, Polypodium mixtum, Polypodium nigrescens* Blume, *Polypodium nipponicum* (i.e., aonekazura' (Japanese)), *Polypodium percussum, Polypodium phymatodes* L., *Polypodium piligerum, Polypodium punctatum* Thunb. ex Murray, *Polypodium pustulatum, Polypodium pycnocarpum* C. Chr., *Polypodium quitense, Polypodium rimbachii, Polypodium* x *rothmaleri* (*P. cambricum* x *P. interjectum*), *Polypodium saximontanum* Windham, *Polypodium scouleri* (Hooker & Greville—coast polypody), *Polypodium scutulatum, Polypodium segregatum, Polypodium* x *shivasiae* Rothm. (*P. cambricum* x *P. interjectum*), *Polypodium sibiricum* Sipliv. (Siberian polypody), *Polypodium triseriale* Swartz, *Polypodium virginianum* L.—rock polypody, *Polypodium vulgare*—common polypody, *Polypodium xalapense*, and any hybrid derived from thereof. More *Polypodium* species and further description of *Polypodium* species can be found in Royal Botanic Garden Edinburgh (RBGE) (2007): Digital Flora *Europaea: Polypodium* species list.; United States Department of Agriculture (2007): Germplasm Resources Information Network—*Polypodium.*; Moore and Bradbury (*Polypodium* to *Lastrea*. Genus I-V, Volume 1 of Natureprinted British Ferns: Being Figures and Descriptions of the Species and Varieties of Ferns Found in the United Kingdom), and Lowe et al. (Ferns: *Gymnogramma, Nothochlaena, Niphobolus, Polypodium*, Groombridge and Sons, 1867), each of which is herein incorporated by reference in its entirety for all purposes.

*Polypodium glycyrrhiza*, commonly known as licorice fern, many-footed fern, and sweet root, is an evergreen fern native to western North America, primarily in a narrow strip in southern Alaska, southwestern Yukon Territory, western British Columbia, Washington, Oregon, and California, though two highly disjunct populations are known from Idaho and Arizona. It thrives in a humid climate, prevailing in areas with cool and moist summers and warm and wet winters. Spores are located in rounded sori on the undersides of the fronds, and are released in cool weather and high humidity. Licorice ferns typically grow epiphytically on living or fallen tree branches, most reoccurring on the species *Acer macrophyllum*, and on rock slabs, as a lithophyte, in coastal forest areas. This species of fern can also be commonly found thriving in substrate covered by moss. *Polypodium glycyrrhiza* grow where conditions are most favorable in terms of nutrients and sunlight, occupying a niche on and oftentimes above costal forest floors. The rhizome, or stem, of the licorice fern develops horizontally beneath the soil, containing a growing tip that gives way to new frond development. The consistency of rhizomes can vary from wood-like hardness to plush-like softness in texture. The inside of the rhizome contains vascular tissue that transports essential minerals, water, and food to the rest of the plant when needed.

The term "inbred", "inbred plant" is used in the context of the present invention. This also includes any single gene conversions of that inbred. The term single allele converted plant as used herein refers to those plants which are developed by a plant breeding technique wherein essentially all of the desired morphological and physiological characteristics of an inbred are recovered in addition to the single allele transferred into the inbred via the breeding technique.

The term "hybrid" refers to any individual cell, tissue or plant resulting from a cross between parents that differ in one or more genes.

The term "offspring" refers to any plant resulting as progeny from a vegetative or sexual reproduction from one or more parent plants or descendants thereof. For instance an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

The term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

In some embodiments, the plants for extraction are grown in a natural environment. In some embodiments, the plants for extraction are grown in a controlled environment, such as a green house. In some embodiments, the plants, plant parts, or plant cells for extraction are grown as tissue culture. In some embodiments, the plants for extraction are grown in more than one environment sequentially during the life circle. In some embodiments, the tissue culture comprises rhizome cells. In some embodiments, the plants for extraction are in the sporophyte stage. In some embodiments, the plants for extraction are in the gametophyte stage. Non-limiting procedures to propagate ferns are described in Ide et al. (Fern horticulture: past, present, and future, Intercept (Jan. 1, 1900), Morel and Wetnore (Fern Callus Tissue Cultur, 38(2): 141-143, American Journal of Botany, 1951), Trigiano and Gray (Plant Tissue Culture Concepts and Laboratory Exercises, Taylor & Francis, 1999), George et al. (Plant Propagation by Tissue Culture, Springer, 2007), each of which is herein incorporated by reference in its entirety for all purposes.

A fern plant producing the compounds of the present invention can be used in a breeding program to produce new varieties or new species with either increased production of one or more interested compounds, or modified ratio among the interested compounds, when compared to the original parent fern plant. The breeding program can also be used to produce new varieties or new species with additional agronomically important traits. As used herein, "agronomically important traits" include any phenotype in a plant or plant part that is useful or advantageous for human use. Examples of agronomically important traits include but are not limited to those that result in increased biomass production, pest resistance, vigor, development time (time to harvest), enhanced nutrient content, novel growth patterns, flavors or colors, salt, heat, drought and cold tolerance, and the like. Variants, mutants and trivial modifications of a fern plant can be generated by methods available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis). For more information of mutagenesis in plants, such as agents, protocols, see Acquaah et al. (Principles of plant genetics and breeding, Wiley-Blackwell, 2007, ISBN 1405136464, 9781405136464), which is herein incorporated by reference in its entity.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Similarly, "Heteroalkylene," "Heteroalkanylene," "Heteroalkenylene" and "Heteroalkynylene," by themselves or as part of other substituents, refer to alkylene, alkanylene, alkenylene and alkynyenel groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{201}$R$^{202}$—, =N—N=, —N=N—, —N=N—NR$^{203}$R$^{204}$, —PR$^{205}$—, —P(O)$_2$—, —POR$^{206}$—, —O—P(O)$_2$—, —SO—, —SO$_2$—, —SnR$^{207}$R$^{208}$— and the like, where R$^{201}$, R$^{202}$, R$^{203}$, R$^{204}$, R$^{205}$, R$^{206}$, R$^{207}$ and R$^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Cycloheteroalkyl," or "Heterocyclyl," by itself or as part of another substituent, refers to a saturated or unsaturated cyclic alkyl radical in which one or more carbon atoms (and optionally any associated hydrogen atoms) are independently replaced with the same or different heteroatom. Similarly, "Cycloheteroalkylene," or "Heterocyclylene," by itself or as part of another substituent, refers to a saturated or unsaturated cyclic alkylene radical in which one or more carbon atoms (and optionally any associated hydrogen atoms) are independently replaced with the same or different heteroatom. The cycloheteroalkyl may be further substituted by one or more heteroatoms including, but not limited to, N, P, O, S, and Si, which attach to the carbon atoms of the cycloheteroalkyl via monovalent or multivalent bond. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, terahydrofuran, tetrahydropyran, imidazolidine, morpholine, piperazine, piperidine, pyrazolidine, pyrrolidone, quinuclidine, and the like. In some embodiments, the cycloheteroalkyl group comprises from 3 to 10 ring atoms (3-10 membered cycloheteroalkyl) In other embodiments, the cycloalkyl group comprise from 5 to 7 ring atoms (5-7 membered cycloheteroalkyl). A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom. In one embodiment, heterocyclyl includes "azacyclyl" which denotes a heterocycle having one or more nitrogen atoms in the ring. An azacyclyl may also contain additional other heteroatom(s), such as oxygen and sulfur. An azacyclyl may be a four, five, six, seven, or eight-membered ring having one or more nitrogen atoms, such as azetidine, imidazolidine, morpholine, piperazine, piperidine, pyrazolidine, pyrrolidone, diazepane, azepane, diazocane, and azocane.

"Amine" refers to a moiety having structural formula of —NH$_2$. "Substituted amine" refers to a moiety having structural formula of —NR$^X$R$^Y$, wherein R$^X$ and R are independently hydrogen (provided that R$^X$ and R$^Y$ are not both hydrogen), alkyl, substituted alkyl, heteroalkyl, substituted heteroalkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, substituted heterocyclyl, acyl, substituted acyl, imine, substituted imine, amidine, e.g., —C(NH)—NH$_2$, or substituted amidine. In one embodiment of —NR$^X$R$^Y$, R$^X$ is hydrogen, and R$^Y$ is alkyl, substituted alkyl, heteroalkyl, substituted heteroalkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, substituted heterocyclyl, acyl, substituted acyl, imine, substituted imine, amidine, e.g., —C(NH)—NH$_2$, or substituted amidine.

"Compound of interest" refers to compound(s) encompassed by structural formulae disclosed herein, such as (I) and (Ia) and includes any subgeneric and specific compounds within these formulae whose structures are disclosed herein. Compound(s) may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. That is, compound(s) of Formula (I) as described herein includes any stereomerically pure or stereomerically enriched compound thereof. The compounds may also exist in several tautomeric forms including the enol form, the keto form and mixtures thereof. Accordingly, the chemical structures depicted herein encompass all possible tautomeric forms of the illustrated compounds. The term "tautomer" as used herein refers to isomers that change into one another with great ease so that they can exist together in equilibrium. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroaryl," by itself or as part of another substituent, refers to a monovalent heteroaromatic or partial heteroaromatic radical derived by the removal of one hydrogen atom from a single atom of a parent heteroaromatic or partial heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. That is, a heteroarylalkyl group is composed of a heteroaryl group connected to an alkylene group which is further attached to other portion of a molecule. The alkylene group in the heteroarylalkyl group can be an alkylene having 1 to 12 carbon atoms, or 1 to 6 carbon atoms, or 1 to 3 carbon atoms. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanylene, alkenylene or alkynylene moiety of the heteroarylalkyl is ($C_1$-$C_6$) alkylene and the heteroaryl moiety is a 5-15-membered heteroaryl. In other embodiments, the heteroarylalkyl is a 6-13 membered heteroarylalkyl, e.g., the alkanylene, alkenylene or alkynylene moiety is ($C_1$-$C_3$) alkylene and the heteroaryl moiety is a 5-10 membered heteroaryl.

"Human taste panel" when referring to a sensory test, as used herein, means sweet flavor or sweet flavor enhancement measurement using human panelists conducting a scaling test. Test samples containing experimental compounds can be compared to a dose-response curve for perceived sweetness intensity of sweeteners (such as, for example, sucralose, sucrose, fructose and other sweeteners) concentrations to determine equivalent sweetness intensity. A group of five to eight, or more, panelists taste solutions including sweeteners at various concentrations, as well as the experimental compound both with and without added sweetener. Panelists then rate sweetness intensity of all samples on a structured horizontal line scale, anchored from 0 to 15, where 0 equals no sweetness and 15 equals equivalent sweetness to a 15% sucrose sample. Scores for sweetness intensity are averaged across panelists. Then using the average scores and/or equation of the line for the sweetener dose-response curve, equivalent sweetness concentrations are determined for the samples containing experimental compounds. An example of the sensory test by human taste panel is described as EXPERIMENT 1 of this application.

The term "isolated" when referring to a compound, as used herein, means separated or isolated away from other components, ingredients, or chemicals which co-exist with the compound of interest regardless whether the other components, ingredients, or chemicals are used or generated when chemically or enzymatically synthesizing the compound of interest, or the other components, ingredients, or chemicals exist with the compound of interest in nature in its native state. In one embodiment, the term "isolated" means that the compound of interest is substantially or essentially freed from components, ingredients, or chemicals that normally accompany it in its native state in licorice fern, i.e., *Polypodium glycyrrhiza*, by at least one purification or other processing step. Such an isolated compound may also be described as substantially pure. The term "substantially pure" as used herein describes a compound of interest that has been separated from components, ingredients, or chemicals that naturally accompany it. In one embodiment, an isolated compound is substantially pure when at least about 50%, at least about 60%, or at least about 70%, or at least about 80%, or at least about 90%, or at least about 95%, or at least about 96%, or at least about 97%, or at least about 98%, or at least about 99% of the total material (by volume, by wet or dry weight, or by mole percent or mole fraction) is the compound of interest. Purity can be measured by any appropriate method, for example by chromatography, gel electrophoresis, or HPLC analysis.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Purified" means having separated a compound of interest from other molecules, including other small molecules (e.g., polypodoside A, polypodoside B, or polypodoside C) and/or macromolecules (e.g., proteins, nucleic acids, and the like), in a manner which increases the percentage of the compound of interest when compared to the percentage of the other molecules subsequent to such separation, such that the compound of interest is present in greater than about 10%, 20%, 30%, 40%, 50%, 60%, 70%, 75%, 80%, 85%, 90%, 95%, 96%, 97%, 98%, or 99% w/w when compared with other molecules. It is understood that the compound of interest may include stereoisomers, including enantiomers and distereomers and/or any or all of the tautomeric forms of the compound of interest, and that these are not necessarily considered other molecules when referring to purification as described herein.

"Stereomerically pure" means a compound of interest that is substantially free of other stereoisomers of that compound. In one embodiment, a stereomerically pure compound of interest may be substantially free of the opposite enantiomer of the compound. In one embodiment, a stereomerically pure compound of interest may be substantially free of other diastereomers of the compound. A typical stereomerically pure compound of interest comprises greater than about 80% by weight of one stereoisomer and less than about 20% by weight of other stereoisomers, more preferably greater than about 90% by weight of one stereoisomer and less than about 10% by weight of the other stereoisomers, even more preferably greater than about 95% by weight of one stereoisomer and less than about 5% by weight of the other, and most preferably greater than about 97% by weight of one stereoisomer and less than about 3% by weight of the other stereoisomers. As used herein and unless otherwise indicated, the term "stereomerically enriched" means a compound of interest, or a composition thereof, that comprises greater than about 60% by weight of one stereoisomer, or greater than about 70% by weight, or greater than about 80% by weight of one stereoisomer. Certain stereomerically pure or stereomerically enriched compound of Formula (I) demonstrate desirable taste profile as described herein.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

"N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N$=O or $R_3N{\rightarrow}O$) or $R_2N^+$—$O^-$ (sometimes written as $R_2N$=O or $R_2N{\rightarrow}O$) when the two R groups are in a heteroaryl ring system.

"Substituted," when used to modify a specified group or radical, means that one or more hydrogen atoms of the specified group or radical are each, independently of one another, replaced with the same or different substituent(s). The term "optionally substituted" means substitued or non-substituted (i.e., unsubstituted). For example, an optionally substituted azacyclic ring means the azacyclic ring can be substituted or nonsubstituted. Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^bR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —OC(O)$R^b$, —OC(S)$R^b$, —OC(O)$O^-$, —OC(O)$OR^b$, —OC(S)$OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)$OR^b$, -alkylene-C(O)$NR^bR^b$, and —$CH_2$—$CH_2$—C(O)—$CH_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —OC(O)$R^b$, —OC(S)$R^b$, —OC(O)$O^-$, —OC(O)$OR^b$, —OC(S)$OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —C(S)OR$^b$, —C(O)NR$^c$R$^c$, —C(NR$^b$)NR$^c$R$^c$, —OC(O)R$^b$, —OC(S)R$^b$, —OC(O)OR$^b$, —OC(S)OR$^b$, —NR$^b$C(O)R$^b$, —NR$^b$C(S)R$^b$, —NR$^b$C(O)R$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined.

Substituent groups from the above lists useful for substituting other specified groups or atoms will be apparent to those of skill in the art.

The above-referenced substituents as represented by chemical formulas are also readily recognized by their chemical names known to one skilled in the art. For example, those substituents include alkyl, heteroalkyl, halo, hydroxyl, alkoxy, amino, alkylamino, cyano, nitro, haloalkyl, carboxylic acid, amide, ester, acyl, thiol, alkylthio, sulfonamide, and etc.

The substituents used to substitute a specified group can be further substituted, typically with one or more of the same or different groups selected from the various groups specified above.

"Vehicle" refers to a diluent, adjuvant, excipient or carrier with which a compound is administered.

As used herein, an "ingestible composition" includes any substance that, either alone or together with another substance, can be taken by mouth whether intended for consumption or not. The ingestible composition includes both "food or beverage products" and "non-edible products". By "Food or beverage products", it is meant any edible product intended for consumption by humans or animals, including solids, semi-solids, or liquids (e.g., beverages). The term "non-edible products" or "noncomestible composition" includes any product or composition that can be taken by humans or animals for purposes other than consumption or as food or beverage. For example, the non-edible product or noncomestible composition includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that may or may not contain any sweetener.

A "ingestibly acceptable carrier or excipient" is a medium and/or composition that is used to prepare a desired dispersed dosage form of the inventive compound, in order to administer the inventive compound in a dispersed/diluted form, so that the biological effectiveness of the inventive compound is maximized. The medium and/or composition may be in any form depending on the intended use of a product, e.g., solid, semi-solid, liquid, paste, gel, lotion, cream, foamy material, suspension, solution, or any combinations thereof (such as a liquid containing solid contents). Ingestibly acceptable carriers includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

An "ingestibly acceptable ingredient" is a substance that is suitable to be taken by mouth and can be combined with a compound described herein to form an ingestible composition. The ingestibly acceptable ingredient may be in any form depending on the intended use of a product, e.g., solid, semi-solid, liquid, paste, gel, lotion, cream, foamy material, suspension, solution, or any combinations thereof (such as a liquid containing solid contents). The ingestibly acceptable ingredient may be artificial or natural. Ingestibly acceptable ingredients includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

Additional ingestibly acceptable ingredients include acids, including, for example citric acid, phosphoric acid, ascorbic acid, sodium acid sulfate, lactic acid, or tartaric acid; bitter ingredients, including, for example caffeine, quinine, green tea, catechins, polyphenols, green *robusta* coffee extract, green coffee extract, whey protein isolate, or potassium chloride; coloring agents, including, for example caramel color, Red #40, Yellow #5, Yellow #6, Blue #1, Red #3, purple carrot, black carrot juice, purple sweet potato, vegetable juice, fruit juice, beta carotene, turmeric curcumin, or titanium dioxide; preservatives, including, for example sodium benzoate, potassium benzoate, potassium sorbate, sodium metabisulfate, sorbic acid, or benzoic acid; antioxidants including, for example ascorbic acid, calcium disodium EDTA, alpha tocopherols, mixed tocopherols, rosemary extract, grape seed extract, resveratrol, or sodium hexametaphosphate; vitamins or functional ingredients including, for example resveratrol, Co-Q10, omega 3 fatty acids, theanine, choline chloride (citocoline), fibersol, inulin (chicory root), taurine, *panax ginseng* extract, guanana extract, ginger extract, L-phenylalanine, L-camitine, L-tartrate, D-glucoronolactone, inositol, bioflavonoids, *Echinacea*, ginko biloba, yerba mate, flax seed oil, garcinia cambogia rind extract, white tea extract, ribose, milk thistle extract, grape seed extract, pyrodixine HCl (vitamin B6), cyanoobalamin (vitamin B12), niacinamide (vitamin B3), biotin, calcium lactate, calcium pantothenate (pantothenic acid), calcium phosphate, calcium carbonate, chromium chloride, chromium polynicotinate, cupric sulfate, folic acid, ferric pyrophosphate, iron, magnesium lactate, magnesium carbonate, magnesium sulfate, monopotassium phosphate, monosodium phosphate, phosphorus, potassium iodide, potassium phosphate, riboflavin, sodium sulfate, sodium gluconate, sodium polyphosphate, sodium bicarbonate, thiamine mononitrate, vitamin D3, vitamin A palmitate, zinc gluconate, zinc lactate, or zinc sulphate; clouding agents, including, for example ester gun, brominated vegetable oil (BVO), or sucrose acetate isobutyrate (SAIB); buffers, including, for example sodium citrate, potassium citrate, or salt; flavors, including, for example propylene glycol, ethyl alcohol, glycerine, gum Arabic (gum acacia), maltodextrin, modified corn starch, dextrose, natural flavor, natural flavor with other natural flavors (natural flavor WONF), natural and artificial flavors, artificial flavor, silicon dioxide, magnesium carbonate, or tricalcium phosphate; and stabilizers, including, for example pectin, xanthan gum, carboxylmethylcellulose (CMC), polysorbate 60, polysorbate 80, medium chain triglycerides, cellulose gel, cellulose gum, sodium caseinate, modified food starch, gum Arabic (gum acacia), or carrageenan.

Some embodiments provide a composition, comprising a bulking agent and one or more compounds having the structure of Formula (I). In some embodiments, the composition comprises between greater than 30% by weight of the bulking agent. In some embodiments, the composition comprises between greater than 40% by weight of the bulking agent. In some embodiments, the composition comprises between greater than 50% by weight of the bulking agent. In some embodiments, the composition comprises between greater than 70% by weight of the bulking agent. In some embodiments, the composition comprises between greater than 90% by weight of the bulking agent.

In some embodiments, the composition comprises between 30% and 99.5% by weight of the bulking agent. In some embodiments, the composition comprises between 30% and 95% by weight of the bulking agent. In some embodiments, the composition comprises between 50% and 99.5% by weight of the bulking agent.

In some embodiments, the bulking agent is selected from the group consisting of maltodextrin, dextro-maltodextrin blends, corn syrup solids, sucrose, fructose, glucose, invert sugar, sorbitol, xylose, ribulose, mannose, mannitol, galactitol, lactitol, isomalt, maltose, tagatose, lactose, inulin, glycerol, propylene glycol, polydextrose, fructooligosaccharides, cellulose, cellulose derivatives, erythritol, and combinations thereof.

In some embodiments, the bulking agent is maltodextrin. In some embodiments, the bulking agent is lactose. In some embodiments, the bulking agent is erythritol. In some embodiments, the bulking agent is mannitol.

In some embodiments, the composition is a tabletop sweetener product, comprising a packet containing the composition. In some embodiments, the packet is a single serving packet. In some embodiments, the packet has a width between 0.2 inches and 2 inches. In some embodiments, the packet has a width between 0.5 inches and 1 inch. In some embodiments, the packet has a length between 1 inch and 5 inches. In some embodiments, the packet has a length between 1.5 inches and 3 inches. In some embodiments, the product comprises between 0.5 g and 3 g of the composition. In some embodiments, the product comprises between 0.75 g and 1.5 g of the composition.

According to the present invention, a chemosensory receptor can be any receptor associated with chemosensory sensation or chemosensory ligand triggered signal transduction, e.g., via taste receptors or taste related receptors expressed in taste bud or internal organs of the body, such as gastrointestinal tract, etc. In one embodiment, a chemosensory receptor is a receptor that belongs to the 7-transmembrane receptor superfamily or G protein-coupled receptors (GPCRs). In another embodiment, a chemosensory receptor is a receptor carrying out signal transduction via one or more G proteins. In yet another embodiment, a chemosensory receptor is a receptor that belongs to family C or class C of GPCRs. In yet another embodiment, a chemosensory receptor is a receptor that belongs to the T1R family. In yet another embodiment, a chemosensory receptor is a receptor of T1R1, T1R2, T1R3, or their equivalences or variances or a combination thereof. In still another embodiment, a chemosensory receptor is a hetero-dimer of T1R2 and T1R3, or their equivalences or variances.

An "enhancer" herein refers to a compound, or an ingestibly acceptable salt or solvate thereof, that modulates (increases) the activation of a particular receptor, preferably the chemosensory, e.g., T1R2/T1R3 receptor. Herein such enhancers will enhance the activation of a chemosensory receptor by its ligand. Typically the "enhancer" will be specific to a particular ligand, i.e., it will not enhance the activation of a chemosensory receptor by chemosensory ligands other than the particular chemosensory ligand or ligands closely related thereto. Some enhancers, at its ligand enhancing concentration, do not result in activation of the particular receptor by themselves. That is, the ligand enhancing concentrations of these enhancers are concentration levels of the enhancers that increase or enhance the activation of a particular receptor by a ligand without substantially activating the particular receptor by the enhancers themselves. In some embodiments, certain enhancers, when used at a concentration higher than the ligand enhancing concentration, can also activate a particular receptor by themselves in addition to modulating (e.g., increase or enhancement) the activation of the receptor. For example, certain enhancers, when used at a concentration higher than the ligand enhancing concentration, can be sweeteners (i.e., sweet flavoring agent/entity) as well. In other embodiments, certain enhancers can activate a particular receptor by themselves in addition to modulating (e.g., increase or enhancement) the activation of the receptor simultaneously at the same concentration. In other words, certain enhancers are also sweeteners (i.e., sweet flavoring agent/entity) at the same time.

A "flavor" herein refers to the perception of taste in a subject, which include sweet, sour, salty, bitter and umami. The subject may be a human or an animal.

A "flavoring agent" herein refers to a compound or the ingestibly acceptable salt or solvate thereof that induces a flavor or taste in an animal or a human. The flavoring agent can be natural, semi-synthetic, or synthetic.

A "flavor modifier" or "flavor modifying agent" herein refers to a compound or the ingestibly acceptable salt or solvate thereof that modulates, including enhancing or potentiating, and/or inducing, the tastes of a flavoring agent in an animal or a human.

A "flavor enhancer" herein refers to a compound or ingestibly acceptable salt thereof that enhances and/or multiplies the tastes of a flavoring agent, or an ingestible composition comprising the flavoring agent.

A "sweet flavor" refers to the sweet taste typically induced by sugar, such as fructose, in an animal or a human.

A "sweet flavoring agent", "sweet flavor entity", "sweetener", or "sweet compound" herein refers to a compound or ingestibly acceptable salt thereof that elicits a detectable sweet flavor in a subject, e.g., fructose or a compound that activates a T1R2/T1R3 receptor in vitro. The subject may be a human or an animal.

A "sweet flavor modifier" or "sweet flavor modifying agent" herein refers to a compound or ingestibly acceptable salt or solvate thereof that modulates, including enhancing or potentiating, inducing, or blocking, the sweet taste of a sweet flavoring agents in an animal or a human. The sweet flavor modifier includes both sweet flavor enhancer and sweet flavoring agent.

A "sweet flavor enhancer" or "sweet flavor enhancing agent" herein refers to an enhancer of a sweet flavor wherein the term enhancer is the same as defined above.

A "sweet receptor activating compound" or "sweet receptor agonist" herein refers to a compound that activates a sweet receptor, such as a T1R2/T1R3 receptor. One example of a sweet receptor activating compound is a sweetener, such as fructose.

A "sweet receptor modulating compound" herein refers to a compound that modulates (activates, block, or enhances/reduces activation of) a sweet receptor such as a T1R2/T1R3 receptor.

A "sweet receptor enhancing compound" herein refers to a compound that enhances or potentiates the effect of a sweet receptor activating compound, e.g., fructose.

The present sweet receptor enhancing compounds or sweet flavor enhancers, at its ligand enhancing concentration of use, may or may not result in activation of the particular receptor by themselves. Some of the sweet receptor enhancing compounds or sweet flavor enhancers, can also activate a particular receptor by themselves in addition to modulating (increase) the activation of the receptor. For example, some of the sweet receptor enhancing compounds or sweet flavor enhancers can also activate a sweet receptor, such as a T1R2/T1R3 receptor, acting as the receptor agonists.

A "sweet flavor modulating amount" herein refers to an amount of a compound of Formula (I) that is sufficient to alter (either increase or decrease) sweet taste in an ingestible composition, or a precursor thereof, sufficiently to be perceived by a human subject. In many embodiments of the invention, at least about 0.001 ppm of the present compound would need to be present in order for most human subjects to perceive a modulation of the sweet flavor of an ingestible composition comprising the present compound. A broad range of concentration that would typically be employed in order to economically provide a desirable degree of sweet flavor modulation can be from about 0.001 ppm to 10,000 ppm, or a narrow range from about 0.1 ppm to about 1,000 ppm. Alternative ranges of sweet flavor modulating amounts can be from about 0.01 ppm to about 3,000 ppm, from about 0.05 ppm to about 1,500 ppm, from about 0.1 ppm to about 500 ppm, or from about 0.1 ppm to about 300 ppm.

A "sweet flavor enhancing amount" herein refers to an amount of a compound that is sufficient to enhance the taste of flavoring agents, e.g., fructose, in a ingestible composition, as perceived by an animal or a human. A broad range of a sweet flavor enhancing amount can be from about 0.001 ppm to 100 ppm, or a narrow range from about 0.1 ppm to about 10 ppm. Alternative ranges of sweet flavor enhancing amounts can be from about 0.01 ppm to about 30 ppm, from about 0.05 ppm to about 15 ppm, from about 0.1 ppm to about 5 ppm, or from about 0.1 ppm to about 3 ppm. In some embodiments, sweet flavor enhancing amount is the amount corresponding to ligand enhancing concentration(s) of a sweet flavor enhancer of the present invention.

A "sweet receptor modulating amount" herein refers to an amount of a compound that is sufficient to modulate (activate, enhance or block) a sweet taste receptor protein. In many embodiments of the invention, a sweet receptor modulating amount is at least about 10 nM, or at least about 100 nM (i.e., about 0.1 µM), or at least about 1 µM, or at least about 10 µM. A "T1R2/T1R3 receptor modulating or activating amount" is an amount of compound that is sufficient to modulate or activate a T1R2/T1R3 receptor. A "sweet receptor" is a taste receptor that can be modulated by a sweet compound. Preferably a sweet receptor is a G protein coupled receptor, and more preferably the sweet receptor is a T1R2/T1R3 receptor.

The "sugar-like" characteristics of the compounds of the present invention include any characteristic similar to that of sucrose and include, but are not limited to, maximal response, flavor profile, temporal profile, adaptation behavior, mouthfeel, concentration/response function, tastant/and flavor/sweet taste interactions, spatial pattern selectivity, and temperature effects. These characteristics are dimensions in which the taste of sucrose is different from the tastes of other compounds. Of these, the flavor profile and temporal profile are particularly important. In a single tasting of a sweet food or beverage, differences (1) in the attributes that constitute a sweetener's flavor profile and (2) in the rates of sweetness onset and dissipation, which constitute a sweetener's temporal profile, between those observed for sucrose and other compounds can be noted.

The flavor profile of a sweetener is a quantitative profile of the relative intensities of all of the taste attributes exhibited. Such profiles often are plotted as histograms or radar plots.

Compounds

In one embodiment, the present invention provides an isolated compound having structural Formula (I):

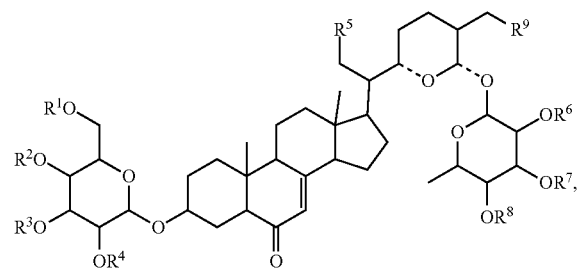

or a salt or solvate thereof; wherein $R^1$, $R^2$, $R^3$, $R^4$, $R^6$, $R^7$, and $R^8$ are independently hydrogen, alkyl, heterocyclyl, or substituted heterocyclyl; and $R^5$ and $R^9$ are independently hydrogen, hydroxyl, alkoxy, heterocyclyl, or substituted heterocyclyl. In one embodiment of Formula (I), $R^5$ is hydrogen, hydroxyl, alkoxy, heterocyclyl, or substituted heterocyclyl; and $R^9$ is hydrogen. In another embodiment of Formula (I), $R^5$ is hydrogen; and $R^9$ is hydrogen, hydroxyl, alkoxy, heterocyclyl, or substituted heterocyclyl. In one embodiment, the heterocyclyl is tetrahydrofuranyl or tetrahydropyranyl; and the substituted heterocyclyl is substituted tetrahydrofuranyl or substituted tetrahydropyranyl. In one embodiment, the substitution comprises multiple hydroxyl substitutions.

In one embodiment, the present invention provides a purified compound having structural Formula (I):

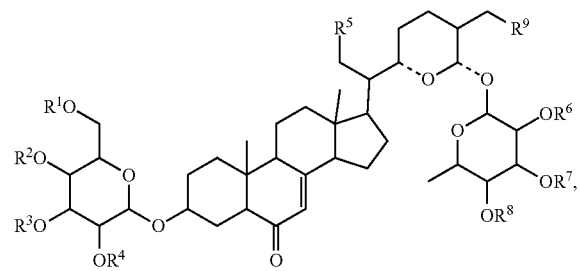

or a salt or solvate thereof; wherein $R^1$, $R^2$, $R^3$, $R^4$, $R^6$, $R^7$, and $R^8$ are independently hydrogen, alkyl, heterocyclyl, or substituted heterocyclyl; and $R^5$ and $R^9$ are independently hydrogen, hydroxyl, alkoxy, heterocyclyl, or substituted heterocyclyl. In one embodiment of Formula (I), $R^5$ is hydrogen, hydroxyl, alkoxy, heterocyclyl, or substituted heterocyclyl; and $R^9$ is hydrogen. In another embodiment of Formula (I), $R^5$ is hydrogen; and $R^9$ is hydrogen, hydroxyl, alkoxy, heterocyclyl, or substituted heterocyclyl. In one embodiment, the heterocyclyl is tetrahydrofuranyl or tetrahydropyranyl; and the substituted heterocyclyl is substituted tetrahydrofuranyl or substituted tetrahydropyranyl. In one embodiment, the substitution comprises multiple hydroxyl substitutions.

In one embodiment of the present invention, the isolated or purified compound of Formula (I) has a purity of about 80% or higher. In another embodiment, the isolated compound of Formula (I) has a purity of about 85% or higher. In another embodiment, the isolated compound of Formula (I) has a purity of about 90% or higher. In another embodiment, the isolated compound of Formula (I) has a purity of about 91%, 92%, 93%, 94%, 95%, 96%, 97%, 98%, or 99%, or higher.

In one embodiment, the present invention provides a *Polypodium glycyrrhiza* extract comprising one or more compounds having structural Formula (I):

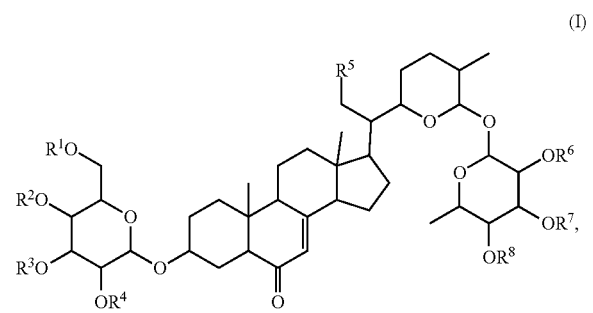

(I)

or a salt or solvate thereof; wherein $R^1$, $R^2$, $R^3$, $R^4$, $R^6$, $R^7$, and $R^8$ are independently hydrogen, alkyl, heterocyclyl, or substituted heterocyclyl; and $R^5$ is hydrogen, hydroxyl, heterocyclyl, or substituted heterocyclyl; and wherein the extract is suitable for human or animal consumption. In one embodiment of Formula (I), $R^5$ is hydrogen, hydroxyl, alkoxy, heterocyclyl, or substituted heterocyclyl; and $R^9$ is hydrogen. In another embodiment of Formula (I), $R^5$ is hydrogen; and $R^9$ is hydrogen, hydroxyl, alkoxy, heterocyclyl, or substituted heterocyclyl. In one embodiment, the heterocyclyl is tetrahydrofuranyl or tetrahydropyranyl; and the substituted heterocyclyl is substituted tetrahydrofuranyl or substituted tetrahydropyranyl. In one embodiment, the substitution comprises multiple hydroxyl substitutions.

In one embodiment, the extract suitable for human or animal consumption by providing an improved taste profile as compared to polypodoside A in a sensory test using a human taste panel. For example, the extract or isolated or purified compound of Formula (I) exhibits reduced off-taste, reduced lingering after-taste, and/or a sugar-like temporal profile including but not limited to sweetness onset, sweetness linger, and/or sugar-like flavor profile in a sensory test using a human taste panel.

Whether or not the extract or isolated or purified compound of Formula (I) exhibits sugar-like characteristics can be determined by any suitable test method. As one skilled in the art would understand, when it comes to perception of tastes and mouthfeel characteristics, there may not be an 'average assessor'. Rather than fight these differences in sensitivity among individuals it is best to take a "crowd-sourcing" approach in action, such as to measure the average response of a group of tasters.

In some embodiments, it is determined by a panel of assessors who taste compositions comprising sugar and compositions comprising the extract or isolated or purified compound of Formula (I), and provide their impression as to the similarities of the characteristics of the sweetener compositions. In some embodiments, the sensory panel consists of expert assessors. In some embodiments, the sensory panel consists of ordinary people assessors. In some embodiments, it is determined by a poll among a given population of human. In some embodiments, the poll consists of randomly elected people. In some embodiments, the sensory panel consists of people who consume sugar at a given quantity and frequency during their life. Today, the average American consumes almost 152 pounds of sugar in one year. This is equal to 3 pounds (or 6 cups) of sugar consumed in one week.

In some embodiments, the extract or isolated or purified compound of Formula (I) is diluted before being tested. In some embodiments, the extract or isolated or purified compound of Formula (I) is diluted for about 2 times, about 5, about 10, about 50, about 100, about 200, about 300, about 400, about 500, about 1000, or more times before being tested.

The tests can be conducted with and/or without additives. In some embodiments, the extract or isolated or purified compound of Formula (I) is tested as a sweet enhancer to one or more additives.

In the test, the participants can provide their impression as to the similarities of the characteristics of the sweetener compositions, with and/or without additives, with those comprising sugar. A suitable procedure for determining whether a composition has a more sugar-like taste is described in embodiments described herein below.

In some embodiments, a panel of assessors is used to measure the reduction of sweetness linger. A panel of assessors generally has 8 to 12 individuals, but can be less or more. In some embodiments, the assessors are screened and trained to evaluate sweetness perception and measure sweetness at several time points from when the sample is initially taken into the mouth, e.g., about 5 seconds, 10 seconds, 20 seconds, 30 seconds, 40 seconds, 50 seconds, 1 minute, 1.5 minutes, 2 minutes, 2.5 minutes, 3 minutes, or more after it has been expectorated. At each time point, a score is given with regard to the similarity between sugar and the extract or isolated or purified compound of Formula (I). For example, a score of 10 means 100% identical flavor profile, as a score of 0 means no similar flavor profile at all. Using statistical analysis, the results are compared between samples containing additives and samples that do not contain additives. A decrease in score for a time point measured after the sample has cleared the mouth indicates there has been a reduction in sweetness perception.

The panel of assessors may be trained using procedures well known to those of ordinary skill in the art. In some embodiments, the focus of training is the recognition of and the measure of sweet. In a particular embodiment, the panel of assessors may be trained using the Spectrum™ Descriptive Analysis Method (Meilgaard et al, Sensory Evaluation Techniques. 3rd edition, Chapter 1), the AROXA™ flavor standards, and/or the comprehensive sensory training kit of SIEBEL Institute of Technology. The training includes, but is not limited to, grading the quality of commercial products and trial samples, assessing the degree to which products conform to pre-defined standards, describing the flavor of an interested compound (qualitatively or quantitatively), determining the degree of similarity between two or more products or batches of products, assessing product shelf life, assessing the quality of raw materials or 'in-process' products, and screening packaging materials for the presence of taints.

In some embodiments, each assessor repeats the measure of the reduction of sweetness linger about one to about five times per sample to ensure accuracy and reproducibility of results. In some embodiments, the assessor takes at least a five minute break between each repetition and/or sample and rinsing well with water to clear the mouth.

In some embodiments, the sample to be tasted is a liquid or solid. In some embodiments, the method of measuring sweetness comprises taking a predetermined amount of sample, such as about 1 mL to about 10 mL or more liquid sample into the mouth, or about 0.1 g to about 10 g of solid sample into the mouth, and holding the sample in the mouth for a predetermined period of time, e.g., for about 1 second, 5 seconds, 10 seconds, 20 seconds, 30 seconds, or more. In some embodiments, the sample is gently swirled in the mouth. In some embodiments, the sample is not swirled in the mouth.

In a non-limiting example of test, after the sample is taken into the mouth, the sweetness intensity perceived at about 1 to 5 seconds is rated. Then the sample is expectorated (without swallowing following expectorating the sample), and the mouth is rinsed with one mouthful of water (e.g., vigorously moving water in mouth as if with mouth wash). After the rinse water is expectorated, the sweetness intensity perceived immediately upon expectorating the rinse water is rated. Then the assessors wait for about half to 1 minute, and while waiting, the assessors can identify the time of maximum perceived sweetness intensity and rate the sweetness intensity at that time, rate the sweetness intensity after another 10 to 30 seconds, rate the sweetness intensity after another 60 seconds (e.g., cumulative 120 seconds after rinse), and rate the sweetness intensity after still another 60 seconds (e.g., cumulative 180 seconds after rinse). Between samples the assessors take a break for about 5-10 minutes, rinsing well with water to clear the mouth.

In some embodiments, the test is a double-blind test. In some embodiments, all assessors are isolated to avoid communication. In some embodiments, assessors are screened before the test in order to identify those with inherent defects in their sensory acuity. The screening also allows the likely response of candidate tasters to training to be predicted, identifying those individuals most likely to perform best after training. For this latter reason, screening may not focus on current competence. For such tests to have the predictive power expected of them, the way in which the training is carried out during the screening phase must be comparable to how it will be done during the training phase.

Guidelines for selection and training of sensory assessors can be found in ISO 8586-1 (Sensory analysis—General guidance for the selection, training and monitoring of assessors—part 1—selected assessors), ISO 8586-1 (Sensory analysis—General guidance for the selection, training and monitoring of assessors—part 2—experts), and ISO 13299—Sensory Analysis (Methodology—General guidance for establishing a sensory profile), and Guidelines for the selection and training of assessors for descriptive analysis—Guideline 37 (CCFRA, 2002), each of which is herein incorporated by reference in its entirety for all purposes.

In one embodiment, the present invention provides a method of preparing a ready-to-use composition, such as a final food or beverage product. The method comprises contacting a first composition, such as a first food or beverage product, with a flavoring concentrate composition or formulation (e.g., solid or liquid) comprising a compound having structural Formula (I), e.g., the isolated or purified compound of Formula (I) or the extract comprising one or more compounds of Formula (I), to form the ready-to-use composition.

In one embodiment, the present invention provides a method of supplying a flavor preparation. The method comprises providing to an entity a flavoring concentrate composition or formulation (e.g., solid or liquid) comprising a compound having structural Formula (I), e.g., the isolated or purified compound of Formula (I) or the extract comprising one or more compounds of Formula (I).

In one embodiment of Formula (I), at least one of $R^1$, $R^2$, $R^3$, and $R^4$ is hydrogen.

In one embodiment of Formula (I), at least one of $R^6$, $R^7$, and $R^8$ is hydrogen.

In one embodiment of Formula (I), Formula (I) does not include the following compound:

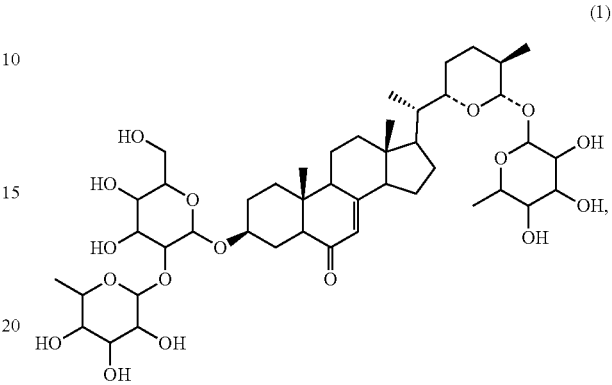

Polypodoside A (1)

Polypodoside B (2)

Polypodoside C (3)

In one embodiment of Formula (I), the compound exhibits increased solubility in water or other aqueous medium or other aqueous medium as compared to polypodoside A. In one embodiment, the compound of Formula (I) is slightly soluble in water or other aqueous medium as defined by The United States Pharmacopeia (USP 26, NF 21, 2003). In one embodiment, the compound of Formula (I) is sparingly soluble in water or other aqueous medium as defined by The United States Pharmacopeia. In one embodiment, the compound of Formula (I) is soluble in water or other aqueous medium as defined by The United States Pharmacopeia. In one embodiment, the compound of Formula (I) is freely soluble in water or other aqueous medium as defined by The United States Pharmacopeia. In one embodiment, the compound of Formula (I) is very soluble in water or other aqueous medium as defined by The United States Pharmacopeia. As such, the compound of Formula (I) is suitable to be processed in laboratory or industrial operations for making various formulations or products.

In one embodiment of the present invention, the compound of Formula (I) is represented by Formula (Ia):

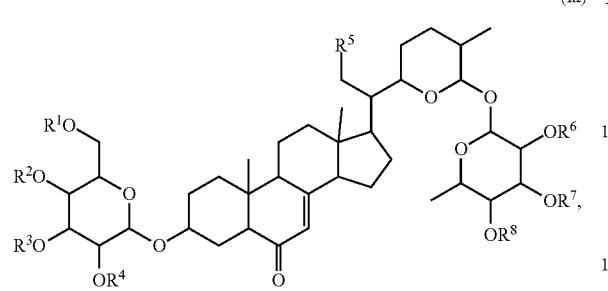

(Ia)

wherein, $R^1$, $R^2$, $R^3$, $R^4$, $R^6$, $R^7$, and $R^8$ are independently hydrogen, alkyl, tetrahydrofuranyl, substituted tetrahydrofuranyl, tetrahydropyranyl, or substituted tetrahydropyranyl; and $R^5$ is hydrogen, hydroxyl, alkoxy, substituted alkoxy, tetrahydrofuranyl, substituted tetrahydrofuranyl, tetrahydropyranyl, or substituted tetrahydropyranyl.

In one embodiment of Formula (Ia), when $R^1$, $R^2$, $R^3$, $R^5$, $R^6$, $R^7$, and $R^8$ are hydrogen; then $R^4$ is not a moiety of 2-methyltetrahydro-2H-pyran-3,4,5-triol.

In one embodiment of Formula (Ia), $R^1$, $R^2$, $R^3$, $R^4$, $R^5$, $R^6$, $R^7$, and $R^8$ are not all hydrogen.

In one embodiment of Formula (Ia), when $R^1$, $R^2$, $R^3$, $R^4$, $R^5$, $R^6$, and $R^8$ are hydrogen; then $R^7$ is not alkyl.

In one embodiment of Formula (Ia), $R^1$ is hydrogen.

In one embodiment of Formula (Ia), $R^3$ is hydrogen.

In one embodiment of Formula (Ia), $R^2$ and $R^4$ are independently hydrogen, heterocyclyl, or substituted heterocyclyl. In one embodiment, the heterocyclyl is tetrahydrofuranyl or tetrahydropyranyl; and the substituted heterocyclyl is substituted tetrahydrofuranyl or substituted tetrahydropyranyl. In one embodiment, the substitution comprises multiple hydroxyl substitutions. In one specific embodiment, the heterocyclyl is a tetrahydropyran moiety, and the substituted heterocyclyl is a substituted tetrahydropyran moiety. For example, the tetrahydropyran moiety can be substituted with one or more groups selected from alkyl, hydroxyl or a substituted tetrahydropyran moiety. In one embodiment, $R^4$ is a substituted tetrahydrofuranyl or substituted tetrahydropyranyl wherein the substitution comprises more than one hydroxyl groups but no alkyl group.

In one embodiment of Formula (Ia), $R^5$ is hydrogen, hydroxyl, or alkoxy.

In one embodiment of Formula (Ia), $R^6$, $R^7$, and $R^8$ are hydrogen.

In one embodiment of the present invention, the compound of Formula (I) or (Ia) is represented by structural Formula (Ib):

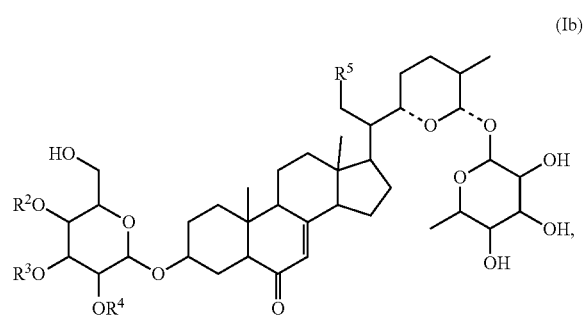

(Ib)

wherein, $R^2$, $R^3$, and $R^4$ are independently hydrogen, heterocyclyl, or substituted heterocyclyl; and $R^5$ is hydrogen, hydroxyl, alkoxy, or substituted alkoxy. In one embodiment, the heterocyclyl is tetrahydrofuranyl or tetrahydropyranyl; and the substituted heterocyclyl is substituted tetrahydrofuranyl or substituted tetrahydropyranyl.

In one embodiment of Formula (Ib), when $R^2$, $R^3$, and $R^5$ are hydrogen; then $R^4$ is not a moiety of 2-methyltetrahydro-2H-pyran-3,4,5-triol.

In one embodiment of Formula (Ib), at least one of $R^2$, $R^3$, $R^4$ and $R^4$ is not hydrogen.

In one embodiment of Formula (Ib), $R^3$ is hydrogen; and $R^2$ and $R^4$ are independently hydrogen or a substituted tetrahydropyran moiety. For example, the tetrahydropyran moiety can be substituted with one or more groups selected from alkyl, hydroxyl, and a substituted tetrahydropyran moiety.

In one embodiment of Formula (Ib), $R^5$ is hydrogen, alkoxy, or substituted alkoxy.

In certain specific embodiments, the compounds of the present invention are selected from the group consisting of (4)

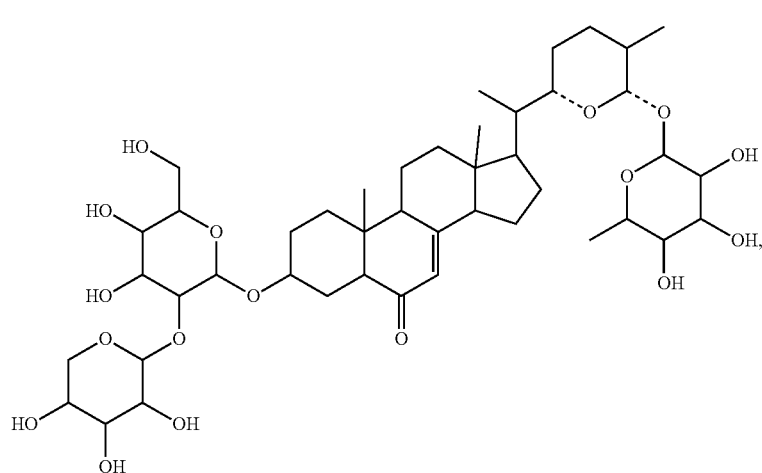

Polypodoside D

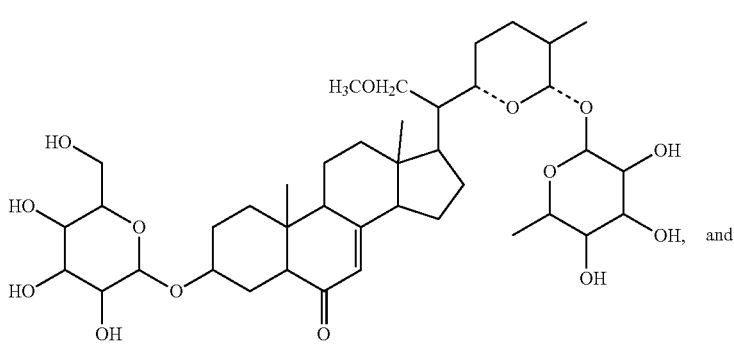

Polypodoside E (5)

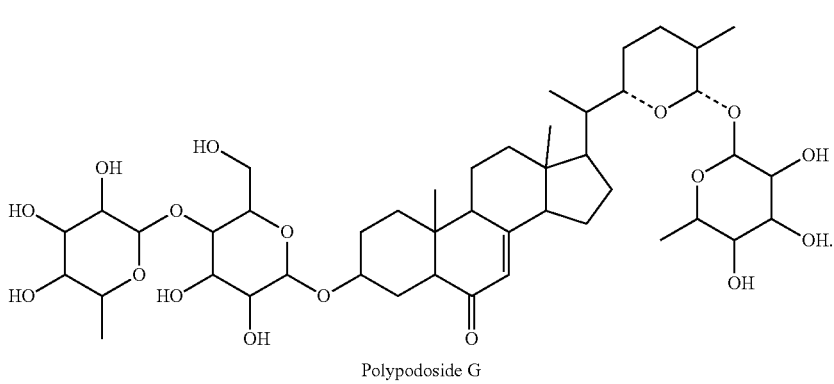

Polypodoside G (7)

Compositions

The present compounds can be used for one or more methods of the present invention, e.g., modifying receptors and their ligands associated with chemosensory or chemosensory related sensation or reaction. According to the present invention, a method of modulating a chemosensory receptor and/or its ligand includes modulating the activity, structure, function, expression, and/or modification of a chemosensory receptor as well as modulating, treating, or taking prophylactic measure of a condition, e.g., physiological or pathological condition, associated with a chemosensory receptor. In general, a physiological or pathological condition associated with a chemosensory receptor includes a condition, disease, or disorder associated with the chemosensory receptor and/or its ligand, e.g., gastrointestinal disorders, metabolic disorders, functional gastrointestinal disorders, etc. In one embodiment, the method includes increasing or enhancing sweet flavor. In another embodiment, the method includes modulating a sweet receptor and/or its ligand expressed in a place of the body other than the taste buds, such as an internal organ. In general, the compounds of the present invention, individually or in combination, can be provided in a composition, such as, e.g., an ingestible composition. In one embodiment, the present compound can impart a more sugar-like temporal profile and/or flavor profile to a sweetener composition by combining one or more present compound with one or more sweetener in the sweetener composition. In another embodiment, the present compound can increase or enhance the sweet taste of a composition by contacting the composition thereof with one or more present compound to form a modified composition. In another embodiment, the present compound can be in a composition that modulates the sweet receptors and/or their ligands expressed in the body other than in the taste buds.

The compounds of Formula (I), (Ia), and its various subgenuses and species, and their salts and/or solvates, should preferably be comestibly acceptable, e.g., deemed suitable for consumption in food or drink from the perspective of giving unmodified comestible compositions an improved and/or pleasing sweet taste, and would not be significantly toxic or causes unpleasant or undesirable pharmacological or toxicological effects on an animal or human at the typical concentrations they are employed as flavoring agents for the comestible compositions.

One of the methods of demonstrating that a flavorant compound is comestibly acceptable is to have the compound tested and/or evaluated by an Expert Panel of the Flavor and Extract Manufacturers Association (FEMA) and declared as to be "Generally Recognized As Safe" ("GRAS"). The FEMA/GRAS evaluation process for flavorant compounds is complex but well known to those of ordinary skill in the food product preparation arts, as is discussed by Smith, et al. in an article entitled "GRAS Flavoring Substances 21," Food Technology, 57(5), pgs 46-59, May 2003, the entire contents of which are hereby incorporated herein by reference. In addition to the FEMA expert panel, an independent, qualified panel of experts in pertinent scientific disciplines may be formed by the manufacturer to evaluate the safety of a specific compound for GRAS status. This process is known as a "self determination of GRAS status." Another method of demonstrating that a flavorant compound is comestibly acceptable is to obtain favorable review by the WHO/FAO Joint Expert Committee on Food Additives, or JECFA. There are also other evaluation methods, such as independent review by the regulatory agency, which are generally known to those of ordinary skill in the food product preparation arts.

In one embodiment, the compounds of the present invention can be used as agonist or at its ligand enhancing concentrations, e.g., very low concentrations on the order of a few parts per million, in combination with one or more known sweeteners, natural or artificial, so as to reduce the concentration of the known sweetener required to prepare an ingestible composition having the desired degree of sweetness.

Commonly used known or artificial sweeteners for use in such combinations of sweeteners include but are not limited to the common saccharide sweeteners, e.g., sucrose, fructose, glucose, and sweetener compositions comprising natural sugars, such as corn syrup (including high fructose corn symp) or other symps or sweetener concentrates derived from natural fruit and vegetable sources, semi-synthetic "sugar alcohol" sweeteners such as erythritol, isomalt, lactitol, mannitol, sorbitol, xylitol, maltodextrin, and the like, and artificial sweeteners such as aspartame, saccharin, acesulfame-K, cyclamate, sucralose, and alitame. Sweeteners also include cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet *Stevia*-based glycosides, carrelame and other guanidine-based sweeteners, etc. The term "sweeteners" also includes combinations of sweeteners as disclosed herein.

In one embodiment, the present compound is added to a noncomestible composition or non-edible product, such as supplements, nutraceuticals, functional food products (e.g., any fresh or processed food claimed to have a health-promoting and/or disease-preventing properties beyond the basic nutritional function of supplying nutrients), pharmaceutical product, over the counter (OTC) product, oral care product, cosmetic products such as sweetened lip balms, and other personal care products.

In general, over the counter (OTC) product and oral care product generally refer to product for household and/or personal use which may be sold without a prescription and/or without a visit to a medical professional. Examples of the OTC products include, but are not limited to Vitamins and dietary supplements; Topical analgesics and/or anesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g., muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral care product include, but are not limited to mouth cleaning strips, toothpaste, toothbrushes, mouthwashes/dental rinses, denture care, mouth fresheners at-home teeth whiteners, dentifrices, and dental floss.

In another embodiment, the present compounds are added to food or beverage products or formulations. Examples of food and beverage products or formulations include, but are not limited to sweet coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionary category generally refers to edible product that is sweet to the taste. Examples of confectionary include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles.

The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary comestible compositions also include breakfast cereals, sweet beverages or solid or liquid concentrate compositions for preparing beverages, ideally so as to enable the reduction in concentration of previously known saccharide sweeteners, or artificial sweeteners.

Typically at least a sweet receptor modulating amount, a sweet receptor ligand modulating amount, a sweet flavor modulating amount, a sweet flavoring agent amount, a sweet flavor enhancing amount, or a therapeutically effective amount of one or more of the present compounds will be added to the ingestible composition, optionally in the presence of known sweeteners, e.g., so that the sweet flavor modified ingestible composition has an increased sweet taste as compared to the ingestible composition prepared without the compounds of the present invention, as judged by human beings or animals in general, or in the case of formulations testing, as judged by a majority of a panel of at least eight human taste testers, via procedures commonly known in the field.

The concentration of sweet flavoring agent needed to modulate or improve the flavor of the ingestible composition will of course depend on many variables, including the specific type of the ingestible composition and its various other ingredients, especially the presence of other known sweet flavoring agents and the concentrations thereof, the natural genetic variability and individual preferences and health conditions of various human beings tasting the compositions, and the subjective effect of the particular compound on the taste of such chemosensory compounds.

One application of the present compounds is for modulating (inducing, enhancing or inhibiting) the sweet taste or other taste properties of other natural or synthetic sweet tastants, and ingestable compositions made therefrom. In one embodiment, the compounds of the present invention is used or provided in its ligand enhancing concentration(s). For example, a broad but also low range of concentrations of the compounds or entities of the present invention would typically be required, i.e., from about 0.1 ppm to 10,000 ppm, or narrower alternative ranges from about 10 ppm to about 1,000 ppm, from about 1 ppm to about 3,000 ppm, from about 5 ppm to about 1,000 ppm, from about 1 ppm to about 500 ppm, or from about 2 ppm to about 200 ppm, or from about 1 ppm to about 100 ppm.

Some embodiments relate to a composition comprising one or more compounds having the structure of Formula (I) or a salt or solvate thereof. In some embodiments, the concentration of the compound in the composition is greater than 100 ppm. In some embodiments, the concentration of the compound is greater than 300 ppm. In some embodiments, the concentration of the compound is greater than 500 ppm. In some embodiments, the concentration of the compound is greater than 800 ppm.

In some embodiments, the concentration of the compound is between 300 ppm and 4000 ppm. In some embodiments, the concentration of the compound is between 300 ppm and 2000 ppm. In some embodiments, the concentration of the compound is between 300 ppm and 1500 ppm. In some embodiments, the concentration of the compound is between 800 ppm and 1500 ppm.

In one embodiment, the present invention provides a sweet enhancing composition. The sweet enhancing composition comprises a compound of the present invention in an amount effective to provide sweetening, e.g., sweet flavor enhancing amount in combination with a first amount of sweetener, wherein the sweetening is more than the sweetening provided by the first amount of sweetener without the compound.

In one embodiment, the present invention provides an ingestible composition which comprises the sweet enhancing composition of the present invention. In certain embodiments, the present ingestible composition is in the form of a food or beverage product, a pharmaceutical composition, a nutritional product, a dietary supplement, over-the-counter medication, or oral care product.

In one embodiment, the present invention provides a sweetener replacement composition which comprises one or more compounds of the present invention in an amount effective to provide sweetening, e.g., at a concentration higher than their ligand enhancing concentration in the absence of a sweetener, e.g., sucrose other than the present compound(s).

According to another aspect of the invention, the compounds of the present invention are provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacture in large industrial scales to produce the ready-to-use soft drinks. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

In one embodiment, the flavoring concentrate formulation comprises i) as flavor modifying ingredient, a compound of the present invention; ii) a carrier; and iii) optionally at least one adjuvant. The term "as flavor modifying ingredient" denotes that the compound of the present invention acts as a flavoring agent or a flavor modifying agent (such as a flavor enhancer) in the formulation. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

In one embodiment, the flavoring concentrate formulation comprises more than about 10% or 15% by weight of a compound of the present invention. In another embodiment, the flavoring concentrate formulation comprises about 20%, 25%, 30%, 35%, or 40% by weight or any amount in between of the present compound. In another embodiment, the flavoring concentrate formulation comprises more than about 40%, 45%, 50%, 55%, 60%, or 65% by weight or any amount in between of the present compound. In another embodiment, the flavoring concentrate formulation comprises more than about 65% by weight of the present compound.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the contents of which are hereby incorporated by reference in its entirety for all purposes.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. The present flavoring concentrate formulation can be carbonated or non-carbonated.

The flavoring concentrate formulation may further comprise a freezing point depressant, nucleating agent, or both as the at least one adjuvant. The freezing point depressant is a ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes a ingestibly acceptable compound or agent which is able to facilitate nucleation. The presence of nucleating agent in the flavoring concentrate formulation can improve the mouthfeel of the frozen slushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

PREPARATIONS AND EXAMPLES

Some exemplary isolation and purificaiton methods useful for preparing the present compounds or the intermediates thereof are described below.

Eight 1-gallon pots of *Polypodium glycyrrhiza* (licorice fern) were obtained from "Keeping it green" nursery located in Stanwood, WA. The plant material was processed by removing the plant soil and washing the plants with water. The rhizomes were separated from the rest of the plant, cut into small pieces and freeze dried for about 5 days. The dried rhizomes (100 g) were weighed out and shredded to a fine consistency in a blender and extracted on ASE in a standard extraction process in multiple cells. The hexanes, EtOAc and MeOH extracts from multiple cells were combined (each step) and evaporated the solvents on genevac to get 5.2 g of hexanes, 1.9 g of EtOAc and 21 g of MeOH extracts.

21 g of the MeOH extract was loaded onto eight 10 g $C_{18}$ samplets (Biotage) using MeOH. Each samplet was loaded into a 60 g $C_{18}$ SNAP column (Biotage) pre-equilibrated at 5% methanol-water. The column was eluted with a step-gradient of water-methanol: 5% methanol→35% methanol→70% methanol→100% methanol (100 mL fractions collected in each step). The solvents were evaporated under reduced pressure and the extracts from eight runs were combined to give 8.9 g of 5%, 6.5 g of 35%, 2.4 g of 70% and 2 g of 100% extracts. The desired compounds eluted in 70 and 100% steps.

The 70 and 100% steps from SPE were fractionated on reversed phase HPLC (30×100 mm Atlantis prep T3 OBD column, 5 um, Waters) by 21 injections (11 runs from 70% and 10 runs from 100% steps, ~210 mg each injection dissolved in 2 mL of DMSO) using an A/B gradient (A=water, B=acetonitrile) of 1→95% B over 50.5 minutes, with a 95% B wash, followed by re-equilibration at 1% (total run time=61 minutes). Each run was collected in 72 tared tubes (12 fractions/plate, 6 plates per run) at 30 mL/fraction. The plates were dried in the Genevac and re-weighed to get the net weight for each fraction. All the frxns were transferred to nunc plates for storage. Polypodoside F (6) and C (3) were isolated and characterized from frxns 34 and 37 of 100% frxn respectively. Polypodoside A, B, D, E and G were co-eluted in frxn 26. Small amount of frxn 26 was further purified on reversed phase HPLC using modified method to isolate Polypodoside G (7).

Frxn 26 from C18 HPLC runs were combined (870 mg) and further purified by HILIC HPLC (30×100 mm BEH amide column, 5 um, Waters) using an A/B gradient (A=100 mM ammonium formate in 3:1 methanol:water, B=acetonitrile) of 90→65% B over 20 minutes, with a 5% B wash, followed by re-equilibration at 90% (total run time=33.2 minutes). Each run was collected in 24 tared tubes (12 fractions/plate, 2 plates per run) at 14 mL/fraction, collection window centered on middle of the desired peak elution. Each parent sample was 28 mg, dissolved in 350 uL methanol and 350 uL acetonitrile. The pooled Fraction 26 from 70 and 100% steps were purified using this procedure.

The plates were dried in the Genevac and re-weighed to get the net weight for each fraction. Each fraction was analyzed on UPLC using the same type of HILIC column (2.1×75 mm, 1.7 um particle, Waters) using a 90→65% B gradient over 5 minutes. Fractions containing the desired peaks with the desired purity were pooled (72 fractions total) and dried under reduced pressure to give a white solid. Polypodoside A was the major compound in the purification process. The minor compounds, polypodoside B, D and E were eluted couple of frxns earlier than polypodoside A. The exemplified compounds were characterized by the spectral data analysis and data comparison with the known Polypodoside isomers in the literature.

Polypodoside D was characterized based on the $^1$H-NMR and LC-MS data in comparison with the close isomer polypodoside A. Polypodoside D was 14 mass units less than polypodoside A, which was also in agreement with the missing of one of the sugar methyl doublets in the $^1$H-NMR spectrum. Based on close spectral comparison, it was clear that one of the sugar units linked at C-3 is either xylose or arabinose in place of rhamnose in polypodoside A.

Spectral Data of Polypodoside A (1):

$^1$H NMR (400 MHz, Pyridine-$d_5$) δ 6.39 (1H, brs, H-1"), 5.86 (1H, brs, H-7), 5.69 (1H, brs, H-1'''), 5.12 (1H, d, J=7.3 Hz, H-1'), 4.50 (1H, d, J=8.4 Hz, H-26), 3.90 (1H, m, H-3), 3.47 (1H, m, H-22), 1.82 (3H, d, J=6.2 Hz, 6"-Me), 1.72 (3H, d, J=6.2 Hz, 6'''-Me), 1.03 (3H, d, J=6.7 Hz, 21-Me), 0.93 (3H, d, J=6.5 Hz, 27-Me), 0.89 (3H, s, 19-Me), 0.49 (3H, s, 18-Me); ESI-MS, 902.61 (M+H$_2$O)+, 885.81 (MH)$^+$, 739.34 (MH$^+$-rhamnose), 577.61 (MH$^+$-rhamnose-glucose); 929.49 (MH$^-$+formate), 883.5 (M−H)$^-$; Molecular formula, $C_{45}H_{72}O_{17}$.

Spectral Data of Polypodoside B (2):

$^1$H NMR (400 MHz, Methanol-$d_4$) δ 5.67 (1H, t, J=2.2 Hz), 4.94 (1H, s), 4.61 (1H, s), 4.44 (1H, d, J=7.8 Hz), 4.22 (1H, d, J=8.4 Hz), 4.00-3.91 (1H, m), 1.21 (3H, d, J=6.2 Hz), 1.01 (3H, d, J=6.7 Hz), 0.90 (3H, d, J=6.5 Hz), 0.87 (3H, s), 0.67 (3H, s); ESI-MS 739.25 (MH)$^+$, 577.29 (MH$^+$- glucose), 431.33 (MH$^+$-glucose—rhamnose); 783.43 (MH$^-$+formate); Molecular formula, $C_{39}H_{62}O_{13}$.

Spectral Data of Polypodoside C (3):

$^1$H NMR (400 MHz, Methanol-$d_4$) δ 5.66 (1H, t, J=2.2 Hz), 5.18 (1H, d, J=1.7 Hz), 4.55 (1H, d, J=7.7 Hz), 4.46 (1H, d, J=3.1 Hz), 4.19-4.05 (1H, m), 3.30 (3H, s), 1.23 (3H, d, J=6.2 Hz), 0.98 (3H, d, J=6.7 Hz), 0.87 (3H, s), 0.86 (3H, d, J=7.6 Hz), 0.67 (3H, s); ESI-MS, 753.55 (MH)$^+$; 797.5 (MH$^-$+formate); Molecular formula, $C_{40}H_{64}O_{13}$.

Spectral Data of Polypodoside D (4):

$^1$H NMR (400 MHz, Pyridine-$d_5$) δ 6.57 (1H, brs, H-1"), 5.85 (1H, brs, H-7), 5.69 (1H, brs, H-1'''), 5.06 (1H, d, J=7.2 Hz, H-1'), 4.50 (1H, d, J=8.4 Hz, H-26), 3.91 (1H, m, H-3), 3.46 (1H, m, H-22), 1.72 (3H, d, J=6.2 Hz, 6'''-Me), 1.03 (3H, d, J=6.7 Hz, 21-Me), 0.93 (3H, d, J=6.4 Hz, 27-Me), 0.85 (3H, s, 19-Me), 0.48 (3H, s, 18-Me); ESI-MS, 871.15 (MH)$^+$, 739.48 (MH$^+$-xylose or arabinose), 577.43 (MH$^+$-xylose or arabinose—glucose), 431.19 (MH$^+$-xylose or arabinose—glucose—rhamnose); 915.56 (MH$^-$+formate), 869.58 (M−H)$^-$; Molecular formula, $C_{44}H_{70}O_{17}$.

Spectral Data of Polypodoside E (5):

$^1$H NMR (400 MHz, Methanol-$d_4$) δ 5.67 (1H, t, J=2.2 Hz), 5.19 (1H, d, J=1.7 Hz), 4.61 (1H, s), 4.55 (1H, d, J=7.7 Hz), 4.13 (1H, dd, J=9.6, 6.2 Hz), 3.93 (1H, dd, J=3.4, 1.7 Hz), 3.66 (3H, s), 1.24 (3H, d, J=6.2 Hz), 1.16 (3H, d, J=7.0 Hz), 0.94 (3H, d, J=6.7 Hz), 0.88 (3H, s), 0.67 (3H, s); ESI-MS, 769.28 (MH)$^+$, 461.26 (MH$^+$-glucose-rhamnose); 813.37 (MH$^-$+formate), 767.24 (M-H)$^-$; Molecular formula, $C_{40}H_{64}O_{14}$.

Spectral Data of Polypodoside F (6):

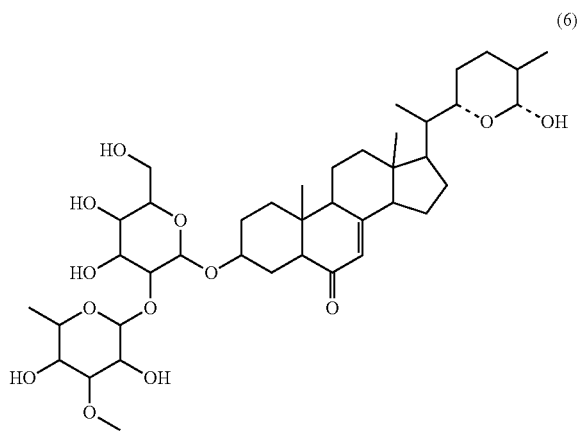

Polypodoside F $^1$H NMR (400 MHz, Methanol-$d_4$) δ 5.67 (1H, t, J=2.2 Hz), 5.19 (1H, d, J=1.7 Hz), 4.55 (1H, d, J=7.7 Hz), 4.39 (1H, d, J=2.2 Hz), 4.13 (1H, dd, J=9.6, 6.2 Hz), 3.95-3.92 (1H, m), 3.42 (3H, s), 1.24 (3H, d, J=6.2 Hz), 1.04 (3H, d, J=6.7 Hz), 0.92 (3H, d, J=6.9 Hz), 0.88 (3H, s), 0.68 (3H, s); ESI-MS, 753.45 (MH)$^+$; 797.5 (MH$^-$+ formate); Molecular formula, $C_{40}H_{64}O_{13}$.

Spectral Data of Polypodoside G (7):

$^1$H NMR (400 MHz, Methanol-$d_4$) δ 5.67 (1H, t, J=2.2 Hz), 5.19 (1H, d, J=1.7 Hz), 4.90 (1H, d, J=1.8 Hz), 4.55 (1H, d, J=7.7 Hz), 4.22 (1H, d, J=8.4 Hz), 4.16-4.10 (1H, m), 1.24 (3H, d, J=6.3 Hz), 1.21 (3H, d, J=6.2 Hz), 1.01 (3H, d, J=6.6 Hz), 0.90 (3H, d, J=6.6 Hz), 0.88 (3H, s), 0.67 (3H, s); ESI-MS, 902.65 (M+H$_2$O)$^+$, 885.68 (MH)$^+$, 739.53 (MH$^+$-rhamnose), 577.47 (MH$^+$-rhamnose-glucose); 929.58 (MH$^-$+ formate), 883.69 (M-H)$^-$; Molecular formula, $C_{45}H_{72}O_{17}$.

Biological Tests

The present isolated compounds have been tested and shown sweet taste modifying activities. Specifically, the present compounds have demonstrated activation of the T1R2/T1R3 receptor as shown in Table 1 below.

TABLE 1

| Compound | EC50 (μm) |
|---|---|
| Polypodoside D | 4.15 |
| Polypodoside E | 18.40 |
| Polypodoside G | 18.70 |

Experiment 1: Sweet Flavor Measurement Using Human Panelists Conducting a Paired Comparison Test Test samples containing experimental compounds were presented in pairs to the human panelist and they were asked to determine which of the sample is sweeter. The present compounds showed sweet flavor enhancement in medium with a wide range of pH value, and this Experiment provided results for samples tested at pH of about 2.8 or 7.1. A group of 10-16 or more panelists participated in each test. Subjects refrained from eating or drinking (except water) for at least 1 hour prior to the test. Subjects rinsed with water several times to clean the mouth.

Taste tests were performed with sucrose or HFCS as the sweetener in the presence or absence of compound. A 0.2% stock solution of compound in water with sodium bicarbonate was prepared and then this stock solution was diluted in the final sample to achieve the targeted final concentration of compound. For the sample evaluated at pH 2.8 the pH of the solution is decreased to about pH 2.8 using citric acid. Taste samples were also prepared in a low sodium phosphate buffer (pH 7.1; "LSB") lacking sucrose or HFCS to evaluate the taste of the compound alone. Low sodium phosphate buffer consists of 0.3 mM KCl, 0.5 mM Na$_2$HPO$_4$, and 0.175 mM KH$_2$PO$_4$. Sample volumes are usually 20 ml.

In one paired comparison test, the panelist was presented with two different samples and asked to identify the sample which is sweeter. The samples within a paired comparison test were presented in a randomized, counterbalanced order. Panelists had up to a 1 minute delay between taste tests to clear the mouth of any tastes.

Binomial probability tables were used to determine the probability of the correct number of responses occurring for each test at alpha=0.05

Test:
Paired comparison taste test for sweetness (0.25 mL sample size)
4% Sucrose vs. LSB+87 ppm Polypodoside D
4% Sucrose vs. 2% Sucrose
4% Sucrose vs. 3% Sucrose Formulation:
All samples made with Low Sodium Buffer (LSB) pH ~7.1 and contain 0% ethanol. Formulation Number=46126088, 43666553, 43666554, 43666555

Conclusions:
Panelists found 4% Sucrose was not significantly different in sweetness than LSB+87 ppm Polypodoside D (p=0.441).
Panelists found 4% Sucrose was significantly sweeter than 2% Sucrose (p=0.001).
Panelists found 4% Sucrose was significantly sweeter than 3% Sucrose (p=0.001).

TABLE 2

Sample selected as sweeter by panelists, n = 42 (14 panelists × 3 reps). Rebaudioside A data is presented as a reference showing 125 ppm Reb A is equivalent to 4% sucrose.
2-AFC Tests with S0168 and Rebaudioside A with Sucrose, pH 7.1

|  | S0168 | | Reb A | |
|---|---|---|---|---|
| Samples | 87 ppm | 100 ppm | 125 ppm | 150 ppm |
| 4% Sucrose | 24 | 28 | 20 | 12 |
| 0% Sucrose + Cmpd | 18 | 8 | 22 | 24 |
| Total | 42 | 36 | 42 | 36 |
| 4% Sucrose selected (p-value) | 0.441 | 0.001 | 0.878 | 0.065 |

These results clearly indicate that Polypodoside D has a sweet taste and demonstrates higher potency than Rebaudioside A in sensory studies.

All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Further Embodiments

1. An isolated compound having structural Formula (I):

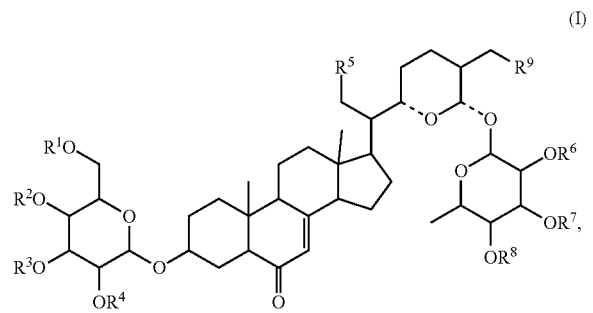

or a salt or solvate thereof; wherein
$R^1$, $R^2$, $R^3$, $R^4$, $R^6$, $R^7$, and $R^8$ are independently hydrogen, alkyl, tetrahydrofuranyl, substituted tetrahydrofuranyl, tetrahydropyranyl, or substituted tetrahydropyranyl; and
$R^5$ and $R^9$ are independently hydrogen, hydroxyl, alkoxy, substituted alkoxy, tetrahydrofuranyl, substituted tetrahydrofuranyl, tetrahydropyranyl, or substituted tetrahydropyranyl; and
with the following provisos:
(a) at least one of $R^1$, $R^2$, $R^3$, and $R^4$ is hydrogen;
(b) at least one of $R^6$, $R^7$, and $R^8$ is hydrogen; and
(c) Formula (I) does not include the following compound:

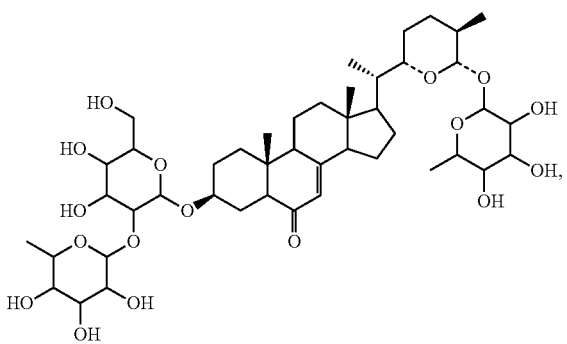

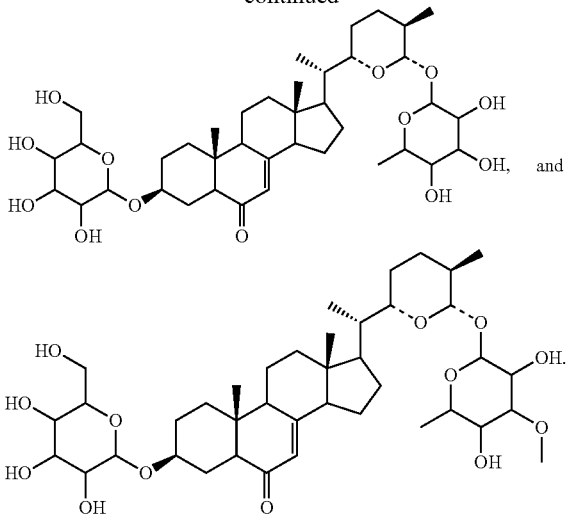

2. The compound of Embodiment 1, which is represented by Formula (Ia):

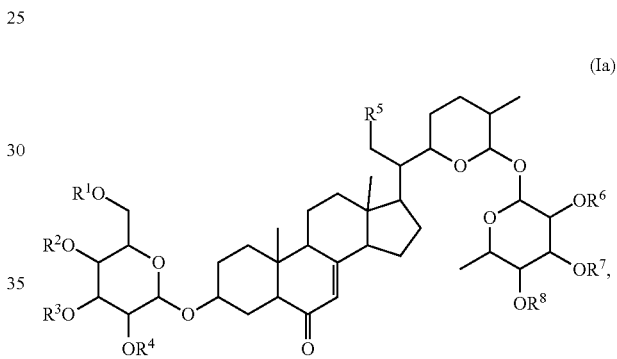

$R^1$, $R^2$, $R^3$, $R^4$, $R^6$, $R^7$, and $R^8$ are independently hydrogen, alkyl, tetrahydrofuranyl, substituted tetrahydrofuranyl, tetrahydropyranyl, or substituted tetrahydropyranyl; and
$R^5$ is hydrogen, hydroxyl, alkoxy, substituted alkoxy, tetrahydrofuranyl, substituted tetrahydrofuranyl, tetrahydropyranyl, or substituted tetrahydropyranyl.

3. The compound of Embodiment 1 or 2, wherein
(a) when $R^1$, $R^2$, $R^3$, $R^5$, $R^6$, $R^7$, and $R^8$ are hydrogen; then $R^4$ is not a moiety of 2-methyltetrahydro-2H-pyran-3,4,5-triol;
(b) $R^1$, $R^2$, $R^3$, $R^4$, $R^5$, $R^6$, $R^7$, and $R^8$ are not all hydrogen; or
(c) when $R^1$, $R^2$, $R^3$, $R^4$, $R^5$, $R^6$, and $R^8$ are hydrogen; then $R^7$ is not alkyl.

4. The compound of any one of Embodiments 1 to 3, wherein $R^1$ is hydrogen.

5. The compound of any one of Embodiments 1 to 4, wherein $R^3$ is hydrogen.

6. The compound of any one of Embodiments 1 to 5, wherein $R^2$ and $R^4$ are independently hydrogen, tetrahydrofuranyl, substituted tetrahydrofuranyl, tetrahydropyranyl, or substituted tetrahydropyranyl.

7. The compound of Embodiment 6, wherein the heterocyclyl is tetrahydropyranyl.

8. The compound of any one of Embodiments 3 to 6, wherein $R^5$ is hydrogen, hydroxyl, alkoxy, or substituted alkoxy.

9. The compound of any one of Embodiments 3 to 8, wherein $R^6$, $R^7$, and $R^8$ are hydrogen.

10. The compound of Embodiment 2, which is represented by structural Formula (Ib):

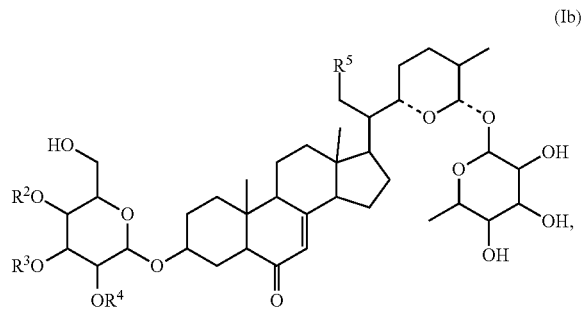

(Ib)

wherein $R^2$, $R^3$, and $R^4$ are independently hydrogen, tetrahydrofuranyl, substituted tetrahydrofuranyl, tetrahydropyranyl, or substituted tetrahydropyranyl; and $R^5$ is hydrogen, hydroxyl, alkoxy, or substituted alkoxy; and with the following provisos:

(a) when $R^2$, $R^3$, and $R^5$ are hydrogen; then $R^4$ is not a moiety of 2-methyltetrahydro-2H-pyran-3,4,5-triol; and (b) at least one of $R^2$, $R^3$, $R^4$ and $R^5$ is not hydrogen.

11. The compound of Embodiment 10, wherein $R^3$ is hydrogen; and $R^2$ and $R^4$ are independently hydrogen or a substituted tetrahydropyranyl.

12. The compound of Embodiment 10 or 11, wherein $R^5$ is hydrogen, alkoxy, or substituted alkoxy.

13. The compound of Embodiment 1, which is selected from the group consisting of

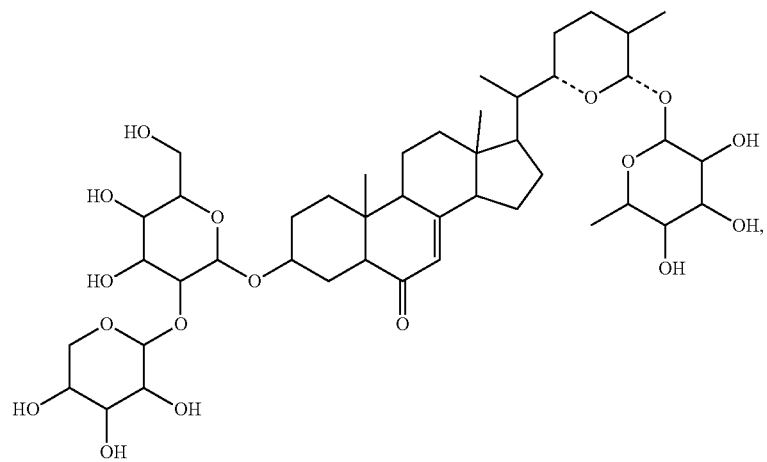

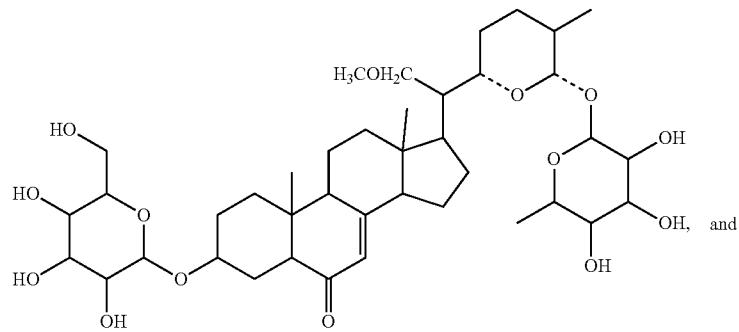

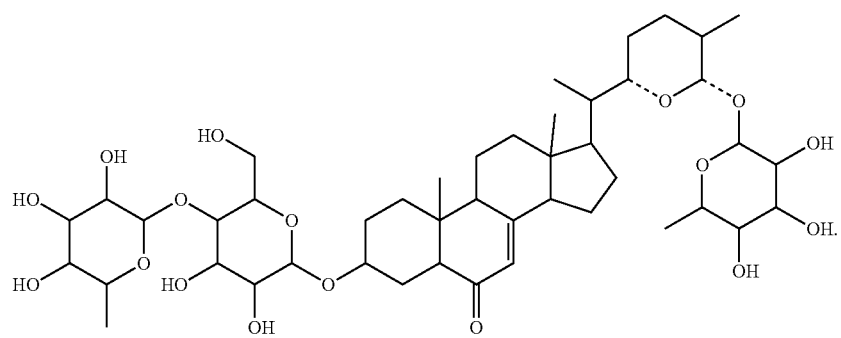

14. A purified compound having structural Formula (I):

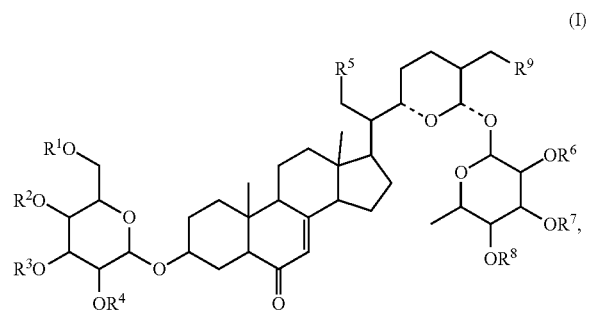

or a salt or solvate thereof; wherein $R^1$, $R^2$, $R^3$, $R^4$, $R^6$, $R^7$, and $R^8$ are independently hydrogen, alkyl, tetrahydrofuranyl, substituted tetrahydrofuranyl, tetrahydropyranyl, or substituted tetrahydropyranyl; and $R^5$ and $R^9$ are independently hydrogen, hydroxyl, alkoxy, substituted alkoxy, tetrahydrofuranyl, substituted tetrahydrofuranyl, tetrahydropyranyl, or substituted tetrahydropyranyl; and with the following provisos:
(a) at least one of $R^1$, $R^2$, $R^3$, and $R^4$ is hydrogen;
(b) at least one of $R^6$, $R^7$, and $R^8$ is hydrogen; and
(c) Formula (I) does not include the following compound:

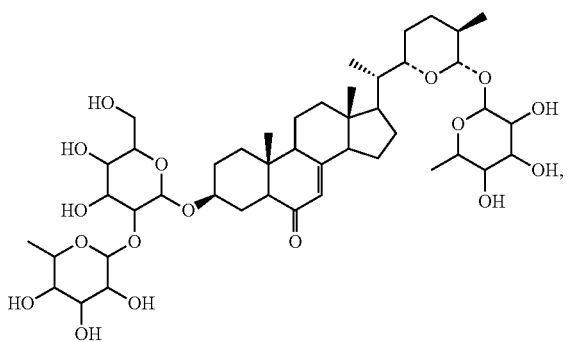

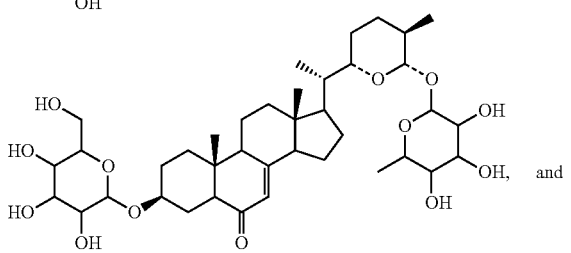

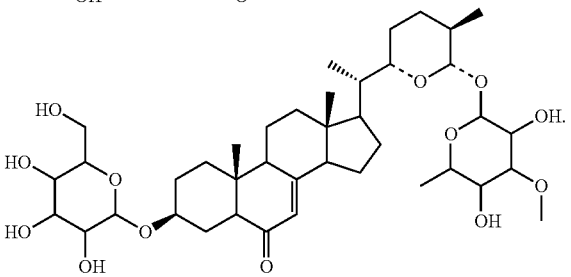

15. The compound of Embodiment 14, which is represented by Formula (Ia):

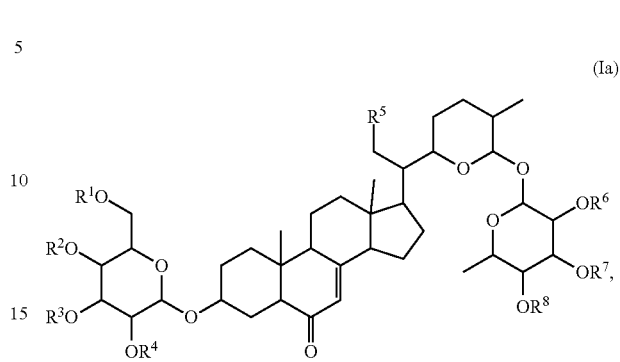

$R^1$, $R^2$, $R^3$, $R^4$, $R^6$, $R^7$, and $R^8$ are independently hydrogen, alkyl, tetrahydrofuranyl, substituted tetrahydrofuranyl, tetrahydropyranyl, or substituted tetrahydropyranyl; and $R^5$ is hydrogen, hydroxyl, alkoxy, substituted alkoxy, tetrahydrofuranyl, substituted tetrahydrofuranyl, tetrahydropyranyl, or substituted tetrahydropyranyl.

16. An extract of a plant in the *Polypodium* genus comprising one or more compounds having structural Formula (I):

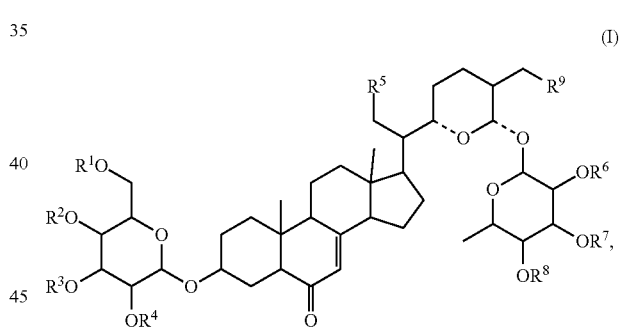

or a salt or solvate thereof; wherein $R^1$, $R^2$, $R^3$, $R^4$, $R^6$, $R^7$, and $R^8$ are independently hydrogen, alkyl, tetrahydrofuranyl, substituted tetrahydrofuranyl, tetrahydropyranyl, or substituted tetrahydropyranyl; and $R^5$ and $R^9$ are independently hydrogen, hydroxyl, alkoxy, substituted alkoxy, tetrahydrofuranyl, substituted tetrahydrofuranyl, tetrahydropyranyl, or substituted tetrahydropyranyl; and with the following provisos:
(a) at least one of $R^1$, $R^2$, $R^3$, and $R^4$ is hydrogen;
(b) at least one of $R^6$, $R^7$, and $R^8$ is hydrogen; and
(c) the extract or Formula (I) does not include the following compound:

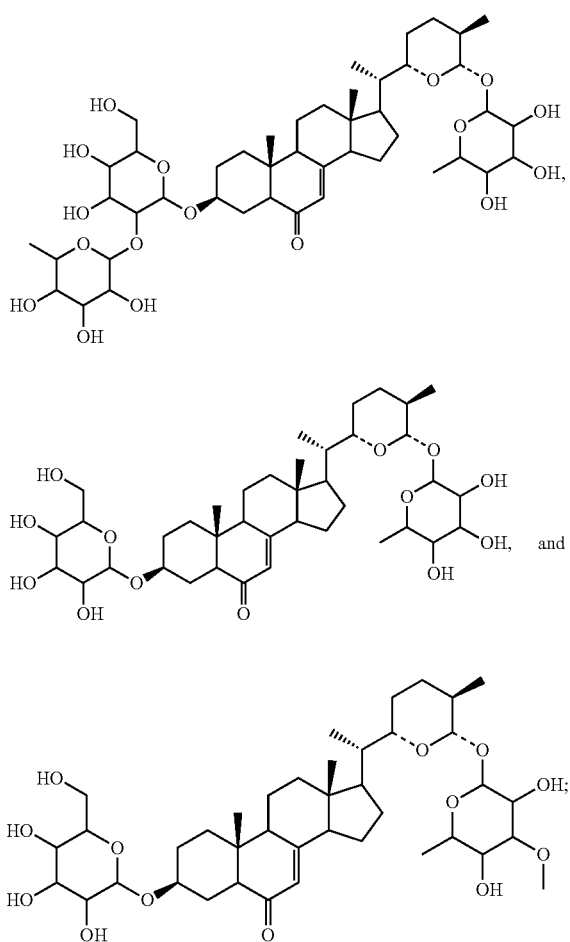

and
wherein the extract is suitable for human or animal consumption.

17. The extract of Embodiment 16, wherein the compound of Formula (I) is represented by Formula (Ia):

(Ia)

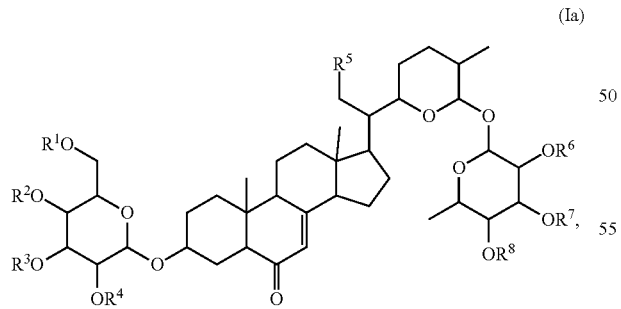

$R^1$, $R^2$, $R^3$, $R^4$, $R^6$, $R^7$, and $R^8$ are independently hydrogen, alkyl, tetrahydrofuranyl, substituted tetrahydrofuranyl, tetrahydropyranyl, or substituted tetrahydropyranyl; and $R^5$ is hydrogen, hydroxyl, alkoxy, substituted alkoxy, tetrahydrofuranyl, substituted tetrahydrofuranyl, tetrahydropyranyl, or substituted tetrahydropyranyl.

18. The extract of Embodiment 16, which exhibits reduced off-taste and/or reduced lingering after-taste as compared to polypodoside A in a sensory test using a human taste panel.

19. The extract of Embodiment 16 or 18, which exhibits a sugar-like temporal profile including sweetness onset, sweetness linger, and/or sugar-like flavor profile in a sensory test using a human taste panel.

20. The extract of any of Embodiments 16 to 19, wherein the plant is *Polypodium glycyrrhiza*.

21. The extract of any of Embodiments 16 to 19, wherein the plant is a whole plant, a plant part, a plant tissue, a plant cell, or a combination thereof.

22. The extract of any of Embodiments 16 to 19, which is obtained from rhizomes of the plant.

23. An ingestible composition, comprising an ingestibly acceptable ingredient and one or more compounds having the structure of Formula (I):

(I)

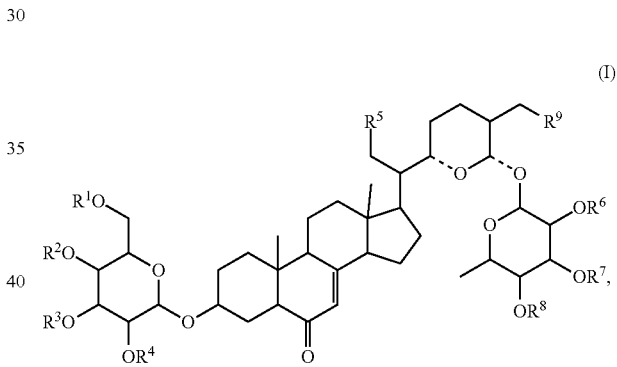

or a salt or solvate thereof; wherein $R^1$, $R^2$, $R^3$, $R^4$, $R^6$, $R^7$, and $R^8$ are independently hydrogen, alkyl, tetrahydrofuranyl, substituted tetrahydrofuranyl, tetrahydropyranyl, or substituted tetrahydropyranyl; and $R^5$ and $R^9$ are independently hydrogen, hydroxyl, alkoxy, substituted alkoxy, tetrahydrofuranyl, substituted tetrahydrofuranyl, tetrahydropyranyl, or substituted tetrahydropyranyl; and with the following provisos:

(a) at least one of $R^1$, $R^2$, $R^3$, and $R^4$ is hydrogen;

(b) at least one of $R^6$, $R^7$, and $R^8$ is hydrogen; and (c) Formula (I) does not include the following compound:

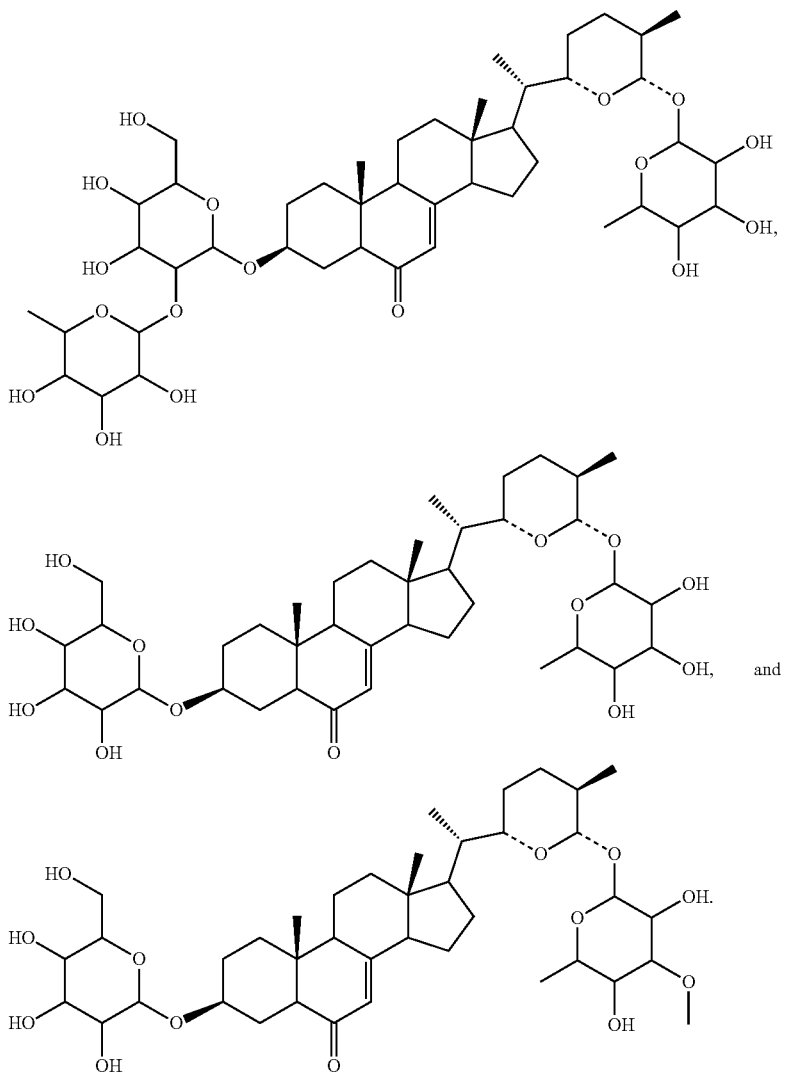

24. The ingestible composition of Embodiment 23, wherein the ingestibly acceptable ingredient comprises vegetable juice, fruit juice, beer, or wine.

25. The ingestible composition of Embodiment 23 wherein the ingestibly acceptable ingredient comprises an acid.

26. The ingestible composition of Embodiment 25, wherein the acid is citric acid or phosphoric acid.

27. The ingestible composition of Embodiment 23, wherein the ingestibly acceptable ingredient comprises one or more of a bitterant, a coloring agent, a preservative, a functional ingredient, a buffer, a natural flavor, an artificial flavor, a food additive, a sour flavorant, one or more fats, oils, or emulsions, and a flour or vegetable powder.

28. The ingestible composition of Embodiment 23, further comprising one or more sweeteners.

29. The ingestible composition of Embodiment 28, wherein the sweetener is selected from the group consisting of sucrose, fructose, glucose, galactose, mannose, lactose, tagatose, maltose, high fructose corn syrup, D-tryptophan, glycine, erythritol, isomalt, lactitol, mannitol, sorbitol, xylitol, maltodextrin, maltitol, isomalt, hydrogenated glucose syrup (HGS), hydrogenated starch hydrolyzate (HSH), stevioside, rebaudioside A, other sweet Stevia-based glycosides, carrelame, other guanidine-based sweeteners, saccharin, acesulfame-K, cyclamate, sucralose, alitame, mogroside, neotame, aspartame, other aspartame derivatives, and combinations thereof.

30. The ingestible composition of Embodiment 23, which has an increased sweet taste as compared to the ingestible composition not containing the compound of any one of Embodiments 1 to 14 or the extract of any one of Embodiments 15 to 19.

31. The ingestible composition of Embodiment 23, which is in form of a food or beverage product, a pharmaceutical composition, a nutritional product, a dietary supplement, over-the-counter medication, or oral care product.

32. The ingestible composition of Embodiment 31, wherein the food or beverage product is for human or animal consumption.

33. The ingestible composition of Embodiment 31, wherein the food or beverage product is selected from the group consisting of the Soup category; the Dried Processed Food category; the Beverage category; the Ready Meal category; the Canned or Preserved Food category; the Frozen Processed Food category; the Chilled Processed Food category; the Snack Food category; the Baked Goods category; the Confectionary category; the Dairy Product category; the Ice Cream category; the Meal Replacement category; the Pasta and Noodle category; the Sauces, Dressings, Condiments category; the Baby Food category; the Spreads category; sweet coatings, frostings, or glazes; and combinations thereof.

34. A composition, comprising one or more compounds having the structure of Formula (I):

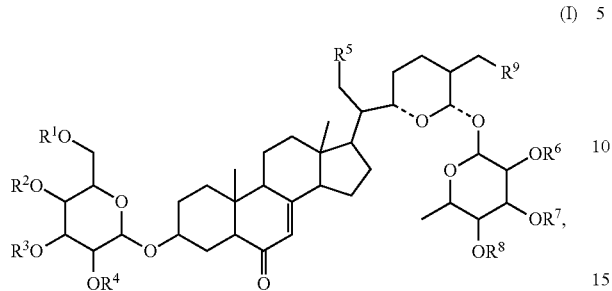

(I)

or a salt or solvate thereof; wherein $R^1$, $R^2$, $R^3$, $R^4$, $R^6$, $R^7$, and $R^8$ are independently hydrogen, alkyl, tetrahydrofuranyl, substituted tetrahydrofuranyl, tetrahydropyranyl, or substituted tetrahydropyranyl; and $R^5$ and $R^9$ are independently hydrogen, hydroxyl, alkoxy, substituted alkoxy, tetrahydrofuranyl, substituted tetrahydrofuranyl, tetrahydropyranyl, or substituted tetrahydropyranyl; and with the following provisos:

(a) at least one of $R^1$, $R^2$, $R^3$, and $R^4$ is hydrogen;

(b) at least one of $R^6$, $R^7$, and $R^8$ is hydrogen; and (c) Formula (I) does not include the following compound:

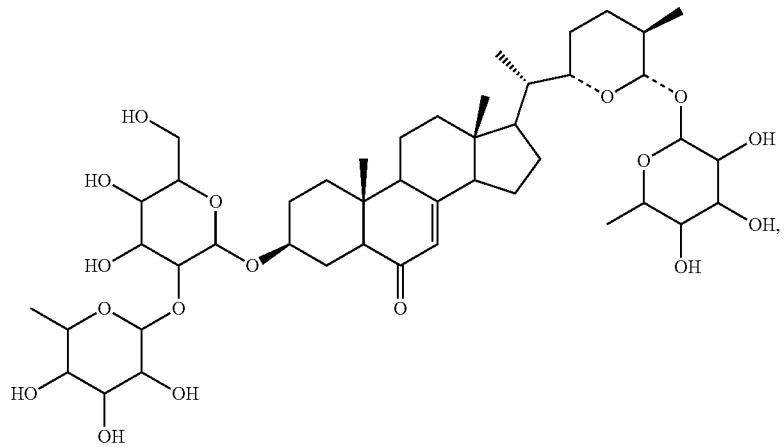

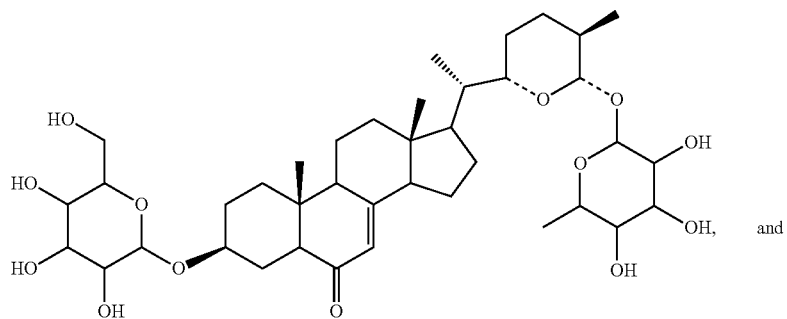

and

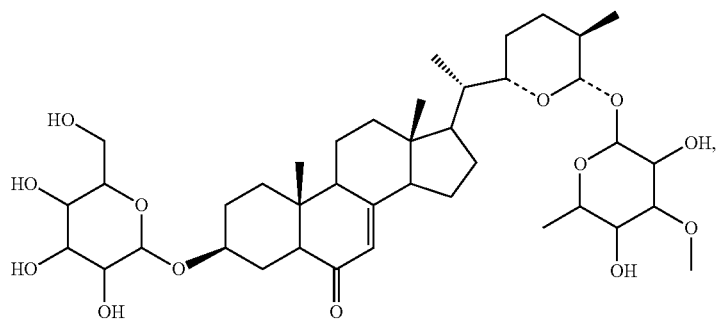

wherein the composition comprises greater than 50% by weight of the compound.

35. The composition of Embodiment 34, comprising greater than 70% by weight of the compound.

36. A composition, comprising a bulking agent and one or more compounds having the structure of Formula (I):

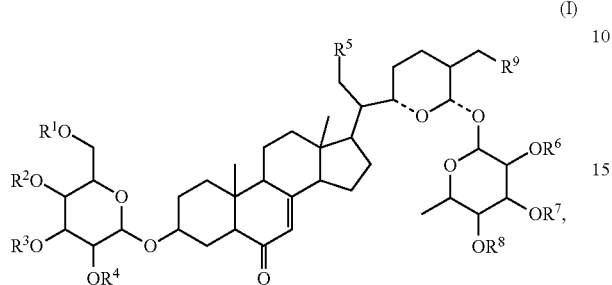

or a salt or solvate thereof; wherein $R^1$, $R^2$, $R^3$, $R^4$, $R^6$, $R^7$, and $R^8$ are independently hydrogen, alkyl, tetrahydrofuranyl, substituted tetrahydrofuranyl, tetrahydropyranyl, or substituted tetrahydropyranyl; and $R^5$ and $R^9$ are independently hydrogen, hydroxyl, alkoxy, substituted alkoxy, tetrahydrofuranyl, substituted tetrahydrofuranyl, tetrahydropyranyl, or substituted tetrahydropyranyl; and with the following provisos:

(a) at least one of $R^1$, $R^2$, $R^3$, and $R^4$ is hydrogen;

(b) at least one of $R^6$, $R^7$, and $R^8$ is hydrogen; and (c) Formula (I) does not include the following compound:

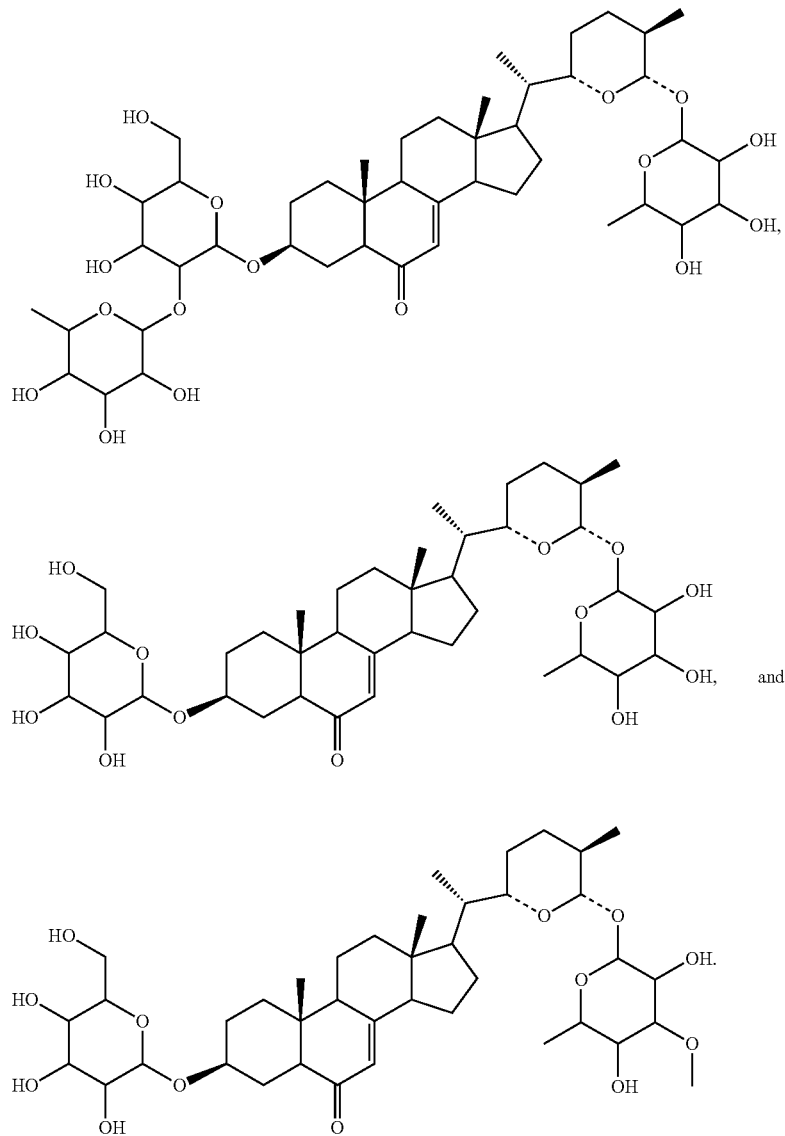

37. The bulking agent of Embodiment 36, comprising greater than 30% by weight of the bulking agent.

38. The bulking agent of Embodiment 36, comprising greater than 50% by weight of the bulking agent.

39. The bulking agent of Embodiment 36, comprising greater than 70% by weight of the bulking agent.

40. The bulking agent of Embodiment 36, comprising greater than 90% by weight of the bulking agent.

41. The composition of any one of Embodiments 36-40, wherein the bulking agent is selected from the group consisting of maltodextrin, dextro-maltodextrin blends, corn syrup solids, sucrose, fructose, glucose, invert sugar, sorbitol, xylose, ribulose, mannose, mannitol, galactitol, lactitol, isomalt, maltose, tagatose, lactose, inulin, glycerol, propylene glycol, polydextrose, fructooligosaccharides, cellulose, cellulose derivatives, erythritol, and combinations thereof 42. The composition of any one of Embodiments 36-40, wherein the bulking agent is selected from maltodextrin, lactose, erythritol, and mannitol.

43. A composition, comprising one or more compounds having the structure of Formula (I):

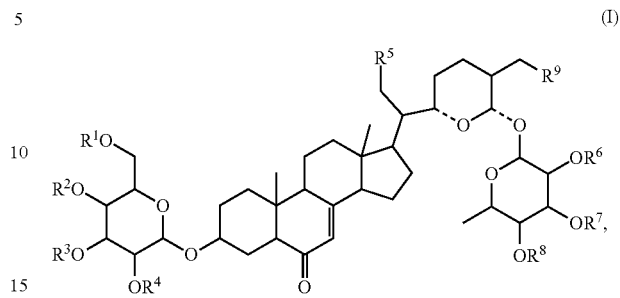

or a salt or solvate thereof; wherein
$R^1$, $R^2$, $R^3$, $R^4$, $R^6$, $R^7$, and $R^8$ are independently hydrogen, alkyl, tetrahydrofuranyl, substituted tetrahydrofuranyl, tetrahydropyranyl, or substituted tetrahydropyranyl; and
$R^5$ and $R^9$ are independently hydrogen, hydroxyl, alkoxy, substituted alkoxy, tetrahydrofuranyl, substituted tetrahydrofuranyl, tetrahydropyranyl, or substituted tetrahydropyranyl; and
with the following provisos:
(a) at least one of $R^1$, $R^2$, $R^3$, and $R^4$ is hydrogen;
(b) at least one of $R^6$, $R^7$, and $R^8$ is hydrogen; and
(c) Formula (I) does not include the following compound:

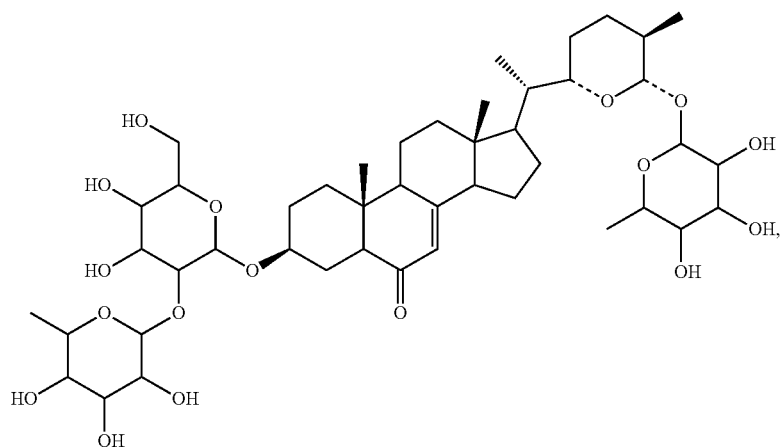

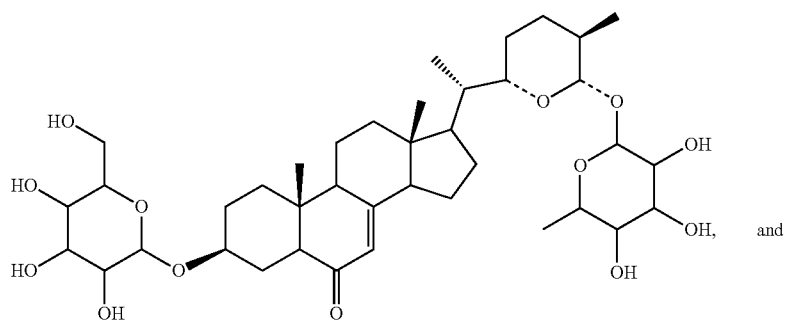

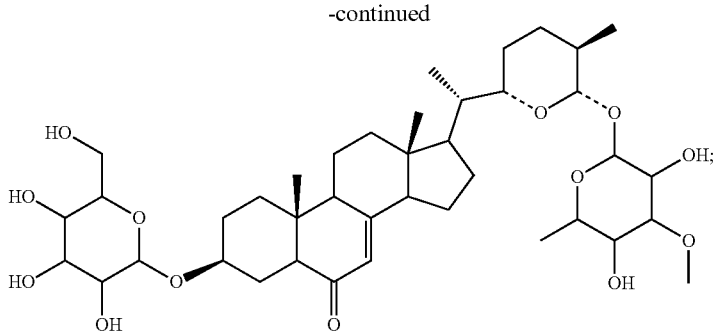

wherein the concentration of the compound in the composition is greater than 100 ppm.

44. The composition of Embodiment 43, wherein the concentration of the compound is between 300 ppm and 4000 ppm.

45. The composition of Embodiment 43, wherein the concentration of the compound is between 300 ppm and 2000 ppm.

46. The composition of Embodiment 43, wherein the concentration of the compound is between 800 ppm and 1500 ppm.

47. A tabletop sweetener product, comprising a packet containing a composition of any one of Embodiments 36-46.

48. The product of Embodiment 47, wherein the packet is a single serving packet.

49. A method of modifying the sweet taste of a composition comprising contacting the composition thereof with an isolated or purified compound of any one of Embodiments 1 to 15 or an extract of any one of Embodiments 16 to 22 to form a sweet taste modified composition.

50. The method of Embodiment 49, wherein the composition comprises one or more sweeteners.

51. A flavoring concentrate formulation comprising
  i) as flavor modifying ingredient, an isolated or purified compound of any one of Embodiments 1 to 15 or an extract of any one of Embodiments 16 to 22;
  ii) a carrier; and
  iii) optionally at least one adjuvant.

52. The flavoring concentrate formulation of Embodiment 51, wherein the at least one adjuvant comprises one or more flavoring agents.

53. The flavoring concentrate formulation of Embodiment 51 or 52, wherein the at least one adjuvant comprises one or more sweeteners.

54. The flavoring concentrate formulation of any one of Embodiments 51 to 53, wherein the at least one adjuvant comprises one or more ingredients selected from the group consisting of a emulsifier, a stabilizer, an antimicrobial preservative, an antioxidant, vitamins, minerals, fats, starches, protein concentrates and isolates, salts, a freezing point depressant, nucleating agent, and combinations thereof.

55. The flavoring concentrate formulation of any one of Embodiments 51 to 54, which is in a form selected from the group consisting of liquid, solid, semi-solid, foamy material, paste, gel, cream, lotion, and combinations thereof.

56. The flavoring concentrate formulation of any one of Embodiments 51 to 55, wherein the compound of any one of Embodiments 1 to 15 or the extract of any one of Embodiments 16 to 22 is in a concentration that is at least 2 times of the concentration in a ready-to-use composition.

57. A method of preparing a ready-to-use composition comprising contacting a first composition with a flavoring concentrate formulation of Embodiment 51 to form the ready-to-use composition.

58. A method of supplying a flavor preparation comprising providing to an entity a flavoring concentrate formulation of Embodiment 51.

We claim:

1. A composition, comprising a bulking agent and one or more

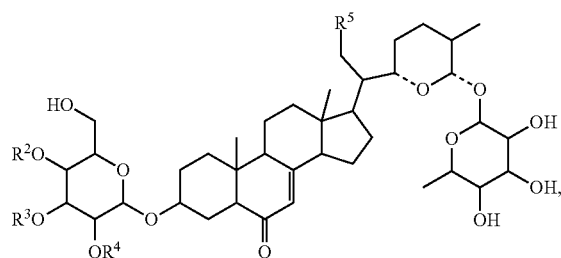

or a salt or solvate thereof; wherein
$R^2$, $R^3$, and $R^4$ are independently hydrogen, tetrahydrofuranyl, substituted tetrahydrofuranyl, tetrahydropyranyl, or substituted tetrahydropyranyl; and
$R^5$ is hydrogen, hydroxyl, alkoxy, or substituted alkoxy; and
with the following provisos:
(a) when $R^2$, $R^3$, and $R^5$ are hydrogen; then $R^4$ is not a moiety of 2-methyltetrahydro-2H-pyran-3,4,5-triol; and
(b) at least one of $R^2$, $R^3$, $R^4$ and $R^5$ is not hydrogen: wherein the compound is not

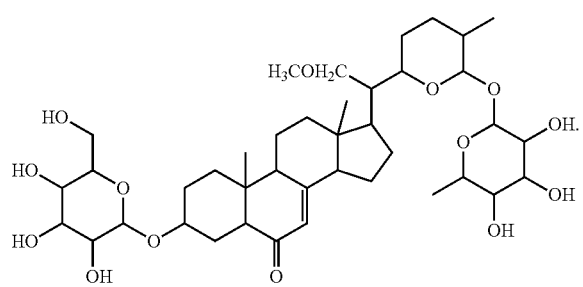

2. The composition of claim 1, wherein $R^3$ is hydrogen.

3. The composition of claim 1, wherein $R^2$ and $R^4$ are independently hydrogen, tetrahydropyranyl, or substituted tetrahydropyranyl.

4. The composition of claim 1, wherein $R^5$ is hydrogen, hydroxyl, or alkoxy.

5. The composition of claim 1, wherein $R^3$ is hydrogen; and $R^2$ and $R^4$ are independently hydrogen or a substituted tetrahydropyranyl.

6. The composition of claim 1, wherein $R^5$ is hydrogen, alkoxy, or substituted alkoxy.

7. The composition of claim 1, in which the one or more compounds are selected from the group consisting of:

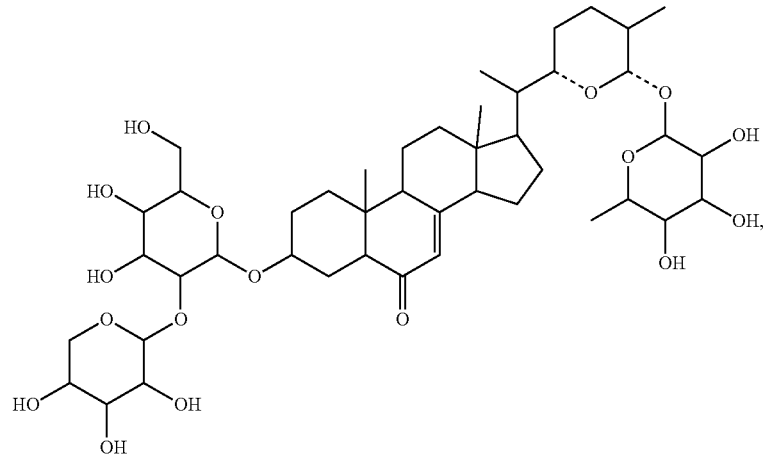

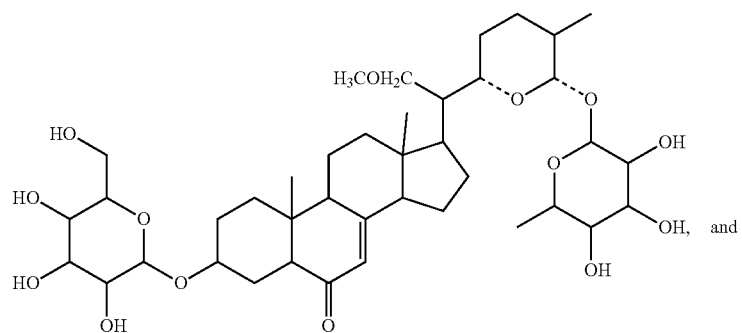

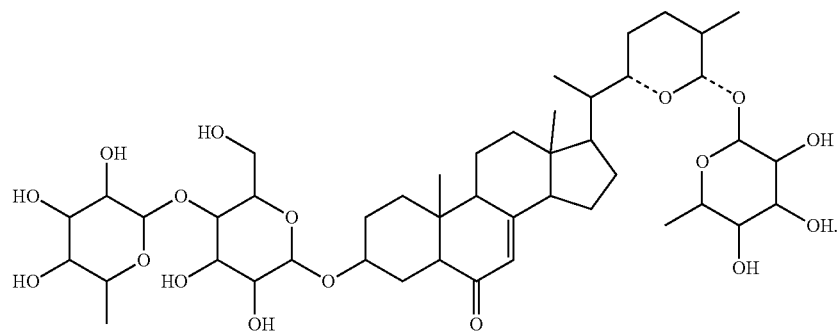

8. An ingestible composition, comprising an ingestibly acceptable ingredient and one or more compounds having the structure of Formula (Ib):

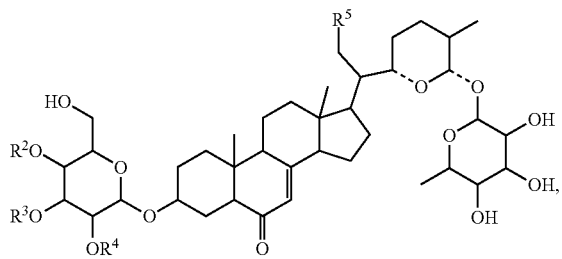

(Ib)

or a salt or solvate thereof; wherein $R^2$, $R^3$, and $R^4$ are independently hydrogen, tetrahydrofuranyl, substituted tetrahydrofuranyl, tetrahydropyranyl, or substituted tetrahydropyranyl; and $R^5$ is hydrogen, hydroxyl, alkoxy, or substituted alkoxy; and with the following provisos:

(a) when $R^2$, $R^3$, and $R^5$ are hydrogen; then $R^4$ is not a moiety of 2-methyltetrahydro-2H-pyran-3,4,5-triol; and (b) at least one of $R^2$, $R^3$, $R^4$ and $R^5$ is not hydrogen: wherein the compound is not

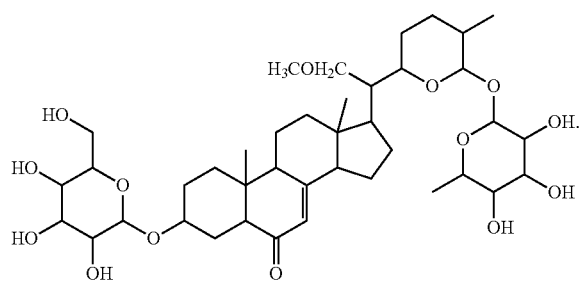

9. The ingestible composition of claim 8, wherein the ingestibly acceptable ingredient comprises vegetable juice, fruit juice, beer, or wine.

10. The ingestible composition of claim 8, further comprising one or more sweeteners.

11. The ingestible composition of claim 8, which is in the form of a food or beverage product, a pharmaceutical composition, a nutritional product, a dietary supplement, over-the-counter medication, or oral care product.

12. The composition of claim 1, comprising greater than 50% by weight of the bulking agent.

13. A composition, comprising one or more compounds having the structure of Formula (Ib):

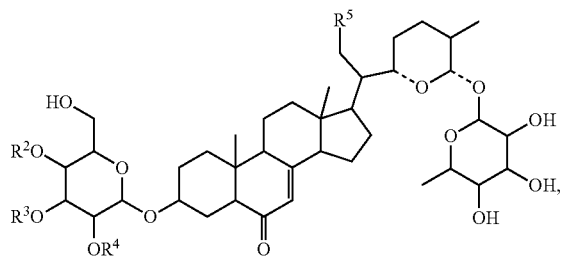

(Ib)

or a salt or solvate thereof; wherein $R^2$, $R^3$, and $R^4$ are independently hydrogen, tetrahydrofuranyl, substituted tetrahydrofuranyl, tetrahydropyranyl, or substituted tetrahydropyranyl; and $R^5$ is hydrogen, hydroxyl, alkoxy, or substituted alkoxy; and with the following provisos:

(a) when $R^2$, $R^3$, and $R^5$ are hydrogen; then $R^4$ is not a moiety of 2-methyltetrahydro-2H-pyran-3,4,5-triol; and (b) at least one of $R^2$, $R^3$, $R^4$ and $R^5$ is not hydrogen wherein the composition comprises greater than 50% by weight of the compound;

wherein the compound is not

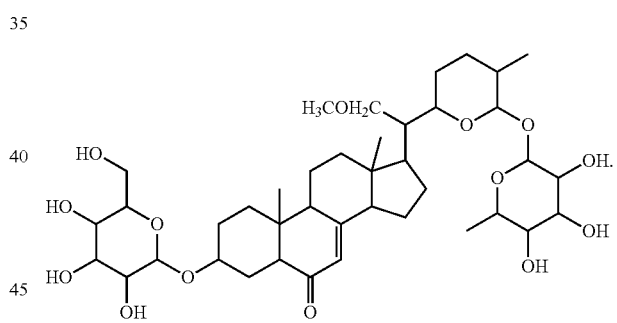

14. The composition of claim 13, comprising greater than 70% by weight of the compound.

* * * * *